US011719637B2

(12) United States Patent
Zhong et al.

(10) Patent No.: US 11,719,637 B2
(45) Date of Patent: *Aug. 8, 2023

(54) BIOSENSORS FOR BIOLOGICAL OR CHEMICAL ANALYSIS AND METHODS OF MANUFACTURING THE SAME

(71) Applicant: ILLUMINA, INC., San Diego, CA (US)

(72) Inventors: Cheng Frank Zhong, San Francisco, CA (US); Hod Finkelstein, El Cerrito, CA (US); Boyan Boyanov, San Diego, CA (US); Dietrich Dehlinger, San Francisco, CA (US); Darren Segale, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 74 days.

This patent is subject to a terminal disclaimer.

(21) Appl. No.: 17/405,379

(22) Filed: Aug. 18, 2021

(65) Prior Publication Data

US 2021/0381977 A1 Dec. 9, 2021

Related U.S. Application Data

(60) Continuation of application No. 16/295,973, filed on Mar. 7, 2019, now Pat. No. 11,181,478, which is a (Continued)

(51) Int. Cl.
*H01L 27/146* (2006.01)
*H01L 27/00* (2006.01)
(Continued)

(52) U.S. Cl.
CPC ...... *G01N 21/645* (2013.01); *B01L 3/502707* (2013.01); *B01L 3/502715* (2013.01);
(Continued)

(58) Field of Classification Search
None
See application file for complete search history.

(56) References Cited

U.S. PATENT DOCUMENTS

| 4,755,667 A | 7/1988 | Marsoner |
| 4,762,413 A | 8/1988 | Namba et al. |

(Continued)

FOREIGN PATENT DOCUMENTS

| CN | 1344366 A | 4/2002 |
| CN | 1875370 A | 12/2006 |

(Continued)

OTHER PUBLICATIONS

Bentley et al., "Accurate whole human genome sequencing using reversible terminator chemistry" Nature vol. 456, pp. 53-59 (Nov. 6, 2008).

(Continued)

*Primary Examiner* — Neil N Turk
(74) *Attorney, Agent, or Firm* — Marshall, Gerstein & Borun LLP

(57) ABSTRACT

Biosensor including a device base having a sensor array of light sensors and a guide array of light guides. The light guides have input regions that are configured to receive excitation light and light emissions generated by biological or chemical substances. The light guides extend into the device base toward corresponding light sensors and have a filter material. The device base includes device circuitry electrically coupled to the light sensors and configured to transmit data signals. A passivation layer extends over the device base and forms an array of reaction recesses above the light guides. The biosensor also includes peripheral crosstalk shields that at least partially surround corresponding light guides of the guide array to reduce optical crosstalk between adjacent light sensors.

19 Claims, 11 Drawing Sheets

Related U.S. Application Data division of application No. 15/175,489, filed as application No. PCT/US2014/069373 on Dec. 9, 2014, now Pat. No. 10,254,225.

(60) Provisional application No. 61/914,275, filed on Dec. 10, 2013.

(51) Int. Cl.

| | | |
|---|---|---|
| *G01N 27/414* | (2006.01) | |
| *B01L 3/00* | (2006.01) | |
| *G01N 33/543* | (2006.01) | |
| *G01N 21/64* | (2006.01) | |
| *H01L 27/088* | (2006.01) | |
| *H01L 29/78* | (2006.01) | |
| *G01N 21/05* | (2006.01) | |
| *C12Q 1/6874* | (2018.01) | |

(52) U.S. Cl.
CPC ..... *G01N 21/6428* (2013.01); *G01N 21/6454* (2013.01); *G01N 27/4145* (2013.01); *G01N 33/54373* (2013.01); *H01L 27/00* (2013.01); *H01L 27/088* (2013.01); *H01L 27/14623* (2013.01); *C12Q 1/6874* (2013.01); *G01N 21/05* (2013.01); *G01N 2021/6441* (2013.01); *G01N 2021/6482* (2013.01); *G01N 2201/061* (2013.01); *G01N 2201/0642* (2013.01)

(56) References Cited

U.S. PATENT DOCUMENTS

| | | |
|---|---|---|
| 5,298,741 A | 3/1994 | Walt |
| 5,315,443 A | 5/1994 | Taira |
| 5,485,277 A * | 1/1996 | Foster .................. G01N 21/648 356/445 |
| 5,605,662 A | 2/1997 | Heller et al. |
| 5,641,658 A | 6/1997 | Adams et al. |
| 5,653,939 A | 8/1997 | Hollis |
| 5,672,881 A | 9/1997 | Striepe |
| 5,843,767 A | 12/1998 | Beattie |
| 5,846,708 A | 12/1998 | Hollis |
| 5,854,684 A | 12/1998 | Stabile |
| 5,872,623 A | 2/1999 | Stabile |
| 5,894,351 A | 4/1999 | Colvin |
| 5,942,775 A | 8/1999 | Yiannoulos |
| 5,965,452 A | 10/1999 | Kovacs |
| 6,090,592 A | 7/2000 | Adams et al. |
| 6,111,248 A | 8/2000 | Melendez |
| 6,117,643 A | 9/2000 | Simpson |
| 6,122,042 A | 9/2000 | Wunderman |
| 6,197,503 B1 * | 3/2001 | Vo-Dinh .............. B01J 19/0046 536/23.1 |
| 6,317,207 B2 | 11/2001 | French |
| 6,323,944 B1 | 11/2001 | Xiao |
| 6,403,970 B1 | 6/2002 | Hung |
| 6,437,345 B1 | 8/2002 | Bruno-Raimondi et al. |
| 6,440,722 B1 | 8/2002 | Knapp et al. |
| 6,441,892 B2 | 8/2002 | Xiao |
| 6,448,064 B1 | 9/2002 | Vo-Dinh |
| 6,458,547 B1 | 10/2002 | Bryan et al. |
| 6,469,785 B1 | 10/2002 | Duveneck |
| 6,485,905 B2 | 11/2002 | Hefti |
| 6,566,805 B1 | 5/2003 | Tsai |
| 6,589,406 B2 | 7/2003 | Mojana |
| 6,653,083 B2 | 11/2003 | Emoto |
| 6,686,150 B1 | 2/2004 | Blackburn |
| 6,693,269 B2 | 2/2004 | Shimizu |
| 6,743,581 B1 | 6/2004 | Dinh |
| 6,784,982 B1 | 8/2004 | Blumenfeld |
| 6,844,563 B2 | 1/2005 | Emoto |
| 6,867,420 B2 | 3/2005 | Mathies |
| 6,867,851 B2 | 3/2005 | Blumenfeld |
| 6,899,137 B2 | 5/2005 | Unger |
| 6,905,834 B1 | 6/2005 | Simpson |
| 6,921,908 B2 | 7/2005 | Reel |
| 6,940,590 B2 | 9/2005 | Colvin |
| 6,946,286 B2 | 9/2005 | Howard |
| 6,975,251 B2 | 12/2005 | Pavicic |
| 6,982,519 B2 | 1/2006 | Guillorn |
| 6,995,386 B2 | 2/2006 | Emoto |
| 7,005,264 B2 | 2/2006 | Su |
| 7,013,033 B2 | 3/2006 | Arena |
| 7,057,026 B2 | 6/2006 | Barnes et al. |
| 7,075,104 B2 | 7/2006 | Fads |
| 7,115,400 B1 | 10/2006 | Adessi et al. |
| 7,145,645 B2 | 12/2006 | Blumenfeld |
| 7,163,822 B2 | 1/2007 | Yazawa |
| 7,170,605 B2 | 1/2007 | Cromwell |
| 7,179,654 B2 | 2/2007 | Verdonk |
| 7,190,445 B2 | 3/2007 | Colvin |
| 7,211,414 B2 | 5/2007 | Hardin et al. |
| 7,221,455 B2 | 5/2007 | Chediak |
| 7,258,731 B2 | 8/2007 | D'Urso et al. |
| 7,280,201 B2 | 10/2007 | Helbing |
| 7,308,292 B2 | 12/2007 | Colvin |
| 7,315,019 B2 | 1/2008 | Turner et al. |
| 7,329,492 B2 | 2/2008 | Hardin et al. |
| 7,349,093 B2 | 3/2008 | Tabata |
| 7,371,538 B2 | 5/2008 | Simpson |
| 7,371,564 B2 | 5/2008 | Kwon |
| 7,405,281 B2 | 7/2008 | Xu et al. |
| 7,413,852 B2 | 8/2008 | Balch |
| 7,414,116 B2 | 8/2008 | Milton et al. |
| 7,416,915 B2 | 8/2008 | Kasano |
| 7,427,673 B2 | 9/2008 | Balasubramanian et al. |
| 7,433,552 B2 | 10/2008 | Kiesel |
| 7,454,296 B2 | 11/2008 | Wang |
| 7,463,353 B2 | 12/2008 | Yershov |
| 7,466,409 B2 | 12/2008 | Scherer |
| 7,489,401 B2 | 2/2009 | Kamei |
| 7,502,123 B2 | 3/2009 | Schmidt |
| 7,524,459 B2 | 4/2009 | Adams |
| 7,541,176 B2 | 6/2009 | Raynor |
| 7,541,444 B2 | 6/2009 | Milton et al. |
| 7,566,537 B2 | 7/2009 | Balasubramanian et al. |
| 7,585,664 B2 | 9/2009 | Chan |
| 7,592,435 B2 | 9/2009 | Milton et al. |
| 7,595,883 B1 | 9/2009 | El Gamal et al. |
| 7,604,981 B1 | 10/2009 | Harris |
| 7,609,379 B2 | 10/2009 | Canioni |
| 7,629,591 B2 | 12/2009 | Nelson |
| 7,638,182 B2 | 12/2009 | D'Urso |
| 7,738,086 B2 | 6/2010 | Shepard |
| 7,750,354 B2 | 7/2010 | Kasano |
| 7,767,441 B2 | 8/2010 | Chiou |
| 7,782,237 B2 | 8/2010 | Ronaghi |
| 7,811,810 B2 | 10/2010 | Chiou |
| 7,812,324 B2 | 10/2010 | Connally |
| 7,839,450 B2 | 11/2010 | Hing |
| 8,696,877 B2 | 4/2014 | Krstajic |
| 9,373,732 B2 | 6/2016 | Velichko |
| 9,799,697 B2 | 10/2017 | Lee |
| 10,254,225 B2 | 4/2019 | Zhong et al. |
| 2002/0055100 A1 | 5/2002 | Kawashima et al. |
| 2002/0145504 A1 | 10/2002 | Vincent |
| 2003/0178641 A1 * | 9/2003 | Blair .................. G01N 21/648 257/200 |
| 2004/0002090 A1 | 1/2004 | Mayer et al. |
| 2004/0096853 A1 | 5/2004 | Mayer |
| 2005/0100900 A1 | 5/2005 | Kawashima et al. |
| 2005/0244870 A1 | 11/2005 | Chee et al. |
| 2006/0068412 A1 | 3/2006 | Tang |
| 2006/0188901 A1 | 8/2006 | Barnes et al. |
| 2006/0240439 A1 | 10/2006 | Smith et al. |
| 2006/0281109 A1 | 12/2006 | Barr Ost et al. |
| 2007/0023799 A1 | 2/2007 | Boettiger |
| 2007/0128624 A1 | 6/2007 | Gormley et al. |
| 2007/0146704 A1 | 6/2007 | Schmidt |
| 2007/0166705 A1 | 7/2007 | Milton et al. |
| 2007/0281288 A1 | 12/2007 | Belkin |
| 2008/0009420 A1 | 1/2008 | Schroth et al. |
| 2008/0039339 A1 | 2/2008 | Hassibi |

(56) References Cited

U.S. PATENT DOCUMENTS

| | | |
|---|---|---|
| 2008/0081769 A1 | 4/2008 | Hassibi |
| 2008/0108082 A1 | 5/2008 | Rank et al. |
| 2008/0176757 A1 | 7/2008 | Hassibi |
| 2008/0203452 A1 | 8/2008 | Moon |
| 2008/0234136 A1 | 9/2008 | Drmanac et al. |
| 2008/0242560 A1 | 10/2008 | Gunderson et al. |
| 2009/0075838 A1 | 3/2009 | El Gamal |
| 2009/0111207 A1 | 4/2009 | Choumane et al. |
| 2009/0127589 A1 | 5/2009 | Rothberg et al. |
| 2009/0197326 A1 | 8/2009 | El Gamal |
| 2009/0244542 A1 | 10/2009 | Cho et al. |
| 2009/0258413 A1 | 10/2009 | Moriwaki |
| 2009/0279093 A1 | 11/2009 | Van Herpen |
| 2009/0284746 A1 | 11/2009 | Klunder |
| 2009/0325164 A1 | 12/2009 | Vossenaar |
| 2010/0015611 A1 | 1/2010 | Webster |
| 2010/0055666 A1 | 3/2010 | Wimberger-Friedl |
| 2010/0065726 A1 | 3/2010 | Zhong et al. |
| 2010/0098311 A1 | 4/2010 | Thon |
| 2010/0108865 A1 | 5/2010 | Cho |
| 2010/0111762 A1 | 5/2010 | Cho |
| 2010/0112342 A1 | 5/2010 | Cho |
| 2010/0122904 A1 | 5/2010 | Hassibi |
| 2010/0200781 A1 | 8/2010 | Khorasani |
| 2010/0204064 A1 | 8/2010 | Cho |
| 2010/0210475 A1 | 8/2010 | Lee |
| 2010/0230610 A1 | 9/2010 | Van Der Zaag |
| 2010/0300895 A1 | 12/2010 | Nobile et al. |
| 2010/0301398 A1 | 12/2010 | Rothberg et al. |
| 2011/0024842 A1 | 2/2011 | Ferraro de Paiva |
| 2011/0059865 A1 | 3/2011 | Smith et al. |
| 2012/0014837 A1 | 1/2012 | Fehr et al. |
| 2012/0019828 A1 | 1/2012 | McCaffrey et al. |
| 2012/0021525 A1 | 1/2012 | Fehr |
| 2012/0052563 A1 | 3/2012 | Liang et al. |
| 2012/0273695 A1 | 11/2012 | Boettiger |
| 2013/0210682 A1 | 8/2013 | Eltoukhy |
| 2014/0274746 A1 | 9/2014 | Khurana et al. |
| 2019/0204225 A1 | 7/2019 | Zhong et al. |

FOREIGN PATENT DOCUMENTS

| | | |
|---|---|---|
| CN | 1922484 A | 2/2007 |
| CN | 101213830 A | 7/2008 |
| CN | 101467027 A | 6/2009 |
| CN | 102203597 A | 9/2011 |
| CN | 102706954 A | 10/2012 |
| CN | 202649594 U | 1/2013 |
| EP | 2221606 | 8/2010 |
| EP | 2207415 | 4/2012 |
| EP | 2459776 | 11/2013 |
| EP | 2772751 | 9/2014 |
| FR | 2913499 A1 | 9/2008 |
| JP | H07-045805 A | 2/1995 |
| JP | 2002-118245 A | 4/2002 |
| JP | 2008-522408 A | 6/2008 |
| JP | 2013-092393 | 5/2013 |
| KR | 10-2009-0079481 A | 7/2009 |
| KR | 10-2010-0091839 A | 8/2010 |
| WO | WO-91/06678 A1 | 5/1991 |
| WO | WO-98/029736 | 7/1998 |
| WO | WO-99/014594 | 3/1999 |
| WO | WO-00/004372 | 1/2000 |
| WO | WO-04/018497 A2 | 3/2004 |
| WO | WO-2005/065814 A1 | 7/2005 |
| WO | WO-2006/064199 A1 | 6/2006 |
| WO | WO-2007/010251 A2 | 1/2007 |
| WO | WO-2007/123744 A2 | 11/2007 |
| WO | WO-2007/135368 A2 | 11/2007 |
| WO | WO-2013/027338 | 2/2013 |

OTHER PUBLICATIONS

Burns, M. et al., "Microfabricated Structures for Integrated DNA Analysis", Proc. Natl. Acad. Sci. Vol. 93, May 1996, 5556-5561.

Caillat, et al., "SA 17.1: Active CMOS Biochips: An Electro-Addressed DNA Probe", 1998, 17.1-17.2.

Caillat, P. et al., "Biochips on CMOS: An Active Matrix Address Array for DNA Analysis", Sensors and Actuators B 61, 1999, 154-162.

Diagnostics, Proceedings of the IEEE, vol. 8, No. 8, Aug. 1998, 1769-1787.

Downs, M., "Prospects for Nucleic Acid Biosensors", Biosensors, Biochemical Society Transactions, vol. 19, 1991.

Eggers, et al., "A Microchip for Quantitative Detection of Molecules Utilizing Luminescent and Radioisotope Reporter Groups", BioTechniques, vol. 17, No. 3, 1994, 516-524.

Eggers, M. et al., "A Review of Microfabricated Devices for Gene-Based Diagnostics", Hematologic Pathology, 9(1), 1995, 1-15.

Eggers, M et al., "A Versatile Biochip for Gene-Based Diagnostics", 1996, 87-92.

International Application No. PCT/US2011/057111, filed on Oct. 20, 2011.

International Search Report for PCT/US2014/069373 dated Apr. 15, 2015.

Kunz, R., "Miniature Integrated Optical Modules for Chemical and Biochemical Sensing", Sensors and Actuators B 39-39, 1997, 13-28.

Kunz, R., "Totally Integrated Optical Measuring Sensors", SPIE vol. 1587 Chemical, Biochemical, and Environmental Fiber Sensors III, 1991, 98-113.

Lamture, et al., "Direct Detection of Nucleic Acid Hybridization on the Surface of a Charge Coupled-Device", Nucleic Acids Research, 22(11), 1994, 2121-2125.

Mastrangelo, C. et al., Microfabricated Devices for Genetic.

Schmalzing, et al., "DNA Typing in Thirty Seconds with a Microfabricated Device", Proc. Natl. Acad. Sci, vol. 9, Sep. 1997, 10273-10278.

U.S. Appl. No. 61/538,294.

U.S. Appl. No. 61/619,878.

U.S. Appl. No. 13/624,200, filed Sep. 21, 2012.

U.S. Appl. No. 61/495,266, filed Jun. 9, 2011.

U.S. Appl. No. 61/552,712, filed Oct. 28, 2011.

Vo-Dinh, T et al., "DNA Biochip Using a Phototransistor Integrated Circuit", Anal. Chem. 1999, 71, Jan. 15, 1999, 358-363.

\* cited by examiner

BIOSENSORS FOR BIOLOGICAL OR CHEMICAL ANALYSIS AND METHODS OF MANUFACTURING THE SAME

CROSS-REFERENCE TO RELATED APPLICATIONS

The present application is continuation of U.S. application Ser. No. 16/295,973, filed Mar. 7, 2019, which is a divisional of U.S. application Ser. No. 15/175,489, filed on Jun. 7, 2016, which is a U.S. National Phase application of International Patent Application No. PCT/US2014/069373, filed on Dec. 9, 2014, which claims the benefit of and priority to U.S. Provisional Application No. 61/914,275, filed on Dec. 10, 2013; each of the aforementioned disclosures is incorporated herein by reference in its entirety.

BACKGROUND

Embodiments of the present disclosure relate generally to biological or chemical analysis and more particularly to systems and methods using detection devices for biological or chemical analysis.

Various protocols in biological or chemical research involve performing a large number of controlled reactions on local support surfaces or within predefined reaction chambers. The designated reactions may then be observed or detected and subsequent analysis may help identify or reveal properties of chemicals involved in the reaction. For example, in some multiplex assays, an unknown analyte having an identifiable label (e.g., fluorescent label) may be exposed to thousands of known probes under controlled conditions. Each known probe may be deposited into a corresponding well of a microplate. Observing any chemical reactions that occur between the known probes and the unknown analyte within the wells may help identify or reveal properties of the analyte. Other examples of such protocols include known DNA sequencing processes, such as sequencing-by-synthesis (SBS) or cyclic-array sequencing.

In some conventional fluorescent-detection protocols, an optical system is used to direct an excitation light onto fluorescently-labeled analytes and to also detect the fluorescent signals that may emit from the analytes. However, such optical systems can be relatively expensive and require a larger benchtop footprint. For example, the optical system may include an arrangement of lenses, filters, and light sources. In other proposed detection systems, the controlled reactions occur immediately over a solid-state imager (e.g., charged-coupled device (CCD) or a complementary metal-oxide-semiconductor (CMOS) detector) that does not require a large optical assembly to detect the fluorescent emissions.

However, the proposed solid-state imaging systems may have some limitations. For example, it may be challenging to distinguish the fluorescent emissions from the excitation light when the excitation light is also directed toward the light sensors of the solid-state imager. In addition, fluidicly delivering reagents to analytes that are located on an electronic device and in a controlled manner may present additional challenges. As another example, fluorescent emissions are substantially isotropic. As the density of the analytes on the solid-state imager increases, it becomes increasingly challenging to manage or account for unwanted light emissions from adjacent analytes (e.g., crosstalk).

BRIEF DESCRIPTION

In an embodiment, a biosensor is provided that includes a flow cell and a detection device having the flow cell coupled thereto. The flow cell and the detection device form a flow channel that is configured to have biological or chemical substances therein that generate light emissions in response to an excitation light. The detection device includes a device base having a sensor array of light sensors and a guide array of light guides. The light guides have input regions that are configured to receive the excitation light and the light emissions from the flow channel. The light guides extend into the device base from the input regions toward corresponding light sensors and have a filter material that is configured to filter the excitation light and permit the light emissions to propagate toward the corresponding light sensors. The device base includes device circuitry electrically coupled to the light sensors and configured to transmit data signals based on photons detected by the light sensors. The detection device also includes a shield layer that extends between the flow channel and the device base. The shield layer has apertures that are positioned relative to the input regions of corresponding light guides such that the light emissions propagate through the apertures into the corresponding input regions. The shield layer extends between adjacent apertures and is configured to block the excitation light and the light emissions incident on the shield layer between the adjacent apertures.

In an embodiment, a biosensor is provided that includes a flow cell and a detection device having the flow cell coupled thereto. The flow cell and the detection device form a flow channel that is configured to have biological or chemical substances therein that generate light emissions in response to an excitation light. The detection device may include a device base having a sensor array of light sensors and a guide array of light guides. The light guides are configured to receive the excitation light and the light emissions from the flow channel. Each of the light guides extends into the device base along a central longitudinal axis from an input region of the light guide toward a corresponding light sensor of the sensor array. The light guides include a filter material that is configured to filter the excitation light and permit the light emissions to propagate therethrough toward the corresponding light sensors. The device base includes device circuitry that is electrically coupled to the light sensors and configured to transmit data signals based on photons detected by the light sensors. The device base includes peripheral crosstalk shields located therein that surround corresponding light guides of the guide array. The crosstalk shields at least partially surround the corresponding light guides about the respective longitudinal axis to reduce optical crosstalk between adjacent light sensors.

In an embodiment, a method of manufacturing a biosensor is provided. The method includes providing a device base having a sensor array of light sensors and device circuitry that is electrically coupled to the light sensors and configured to transmit data signals based on photons detected by the light sensors. The device base has an outer surface. The method also includes applying a shield layer to the outer surface of the device base and forming apertures through the shield layer. The method also includes forming guide cavities that extend from corresponding apertures toward a corresponding light sensor of the sensor array and depositing filter material within the guide cavities. A portion of the filter material extends along the shield layer. The method also includes curing the filter material and removing the filter material from the shield layer. The filter material within the guide cavities forms light guides. The method also includes applying a passivation layer to the shield layer such that the passivation layer extends directly along the shield layer and across the apertures.

In an embodiment, a bio sensor is provided that includes a device base having a sensor array of light sensors and a guide array of light guides. The device base has an outer surface. The light guides have input regions that are configured to receive excitation light and light emissions generated by biological or chemical substances proximate to the outer surface. The light guides extend into the device base from the input regions toward corresponding light sensors and have a filter material that is configured to filter the excitation light and permit the light emissions to propagate toward the corresponding light sensors. The device base includes device circuitry electrically coupled to the light sensors and configured to transmit data signals based on photons detected by the light sensors. The biosensor also includes a shield layer that extends along the outer surface of the device base. The shield layer has apertures that are positioned relative to the input regions of corresponding light guides such that the light emissions propagate through the apertures into the corresponding input regions. The shield layer extends between adjacent apertures and is configured to block the excitation light and the light emissions incident on the shield layer between the adjacent apertures.

In an embodiment, a bio sensor is provided that includes a device base having a sensor array of light sensors and a guide array of light guides. The device base has an outer surface. The light guides are configured to receive excitation light and light emissions generated by biological or chemical substances proximate to the outer surface. Each of the light guides extends into the device base along a central longitudinal axis from an input region of the light guide toward a corresponding light sensor of the sensor array. The light guide includes a filter material that is configured to filter the excitation light and permit the light emissions to propagate therethrough toward corresponding light sensors. The device base includes device circuitry electrically coupled to the light sensors and configured to transmit data signals based on photons detected by the light sensors. The device base includes peripheral crosstalk shields located therein that surround corresponding light guides of the guide array. The crosstalk shields at least partially surrounding the corresponding light guides about the respective longitudinal axis to at least one of block or reflect errant light rays to reduce optical crosstalk between adjacent light sensors.

While multiple embodiments are described, still other embodiments of the described subject matter will become apparent to those skilled in the art from the following detailed description and drawings, which show and describe illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

DETAILED DESCRIPTION

Figure 1:
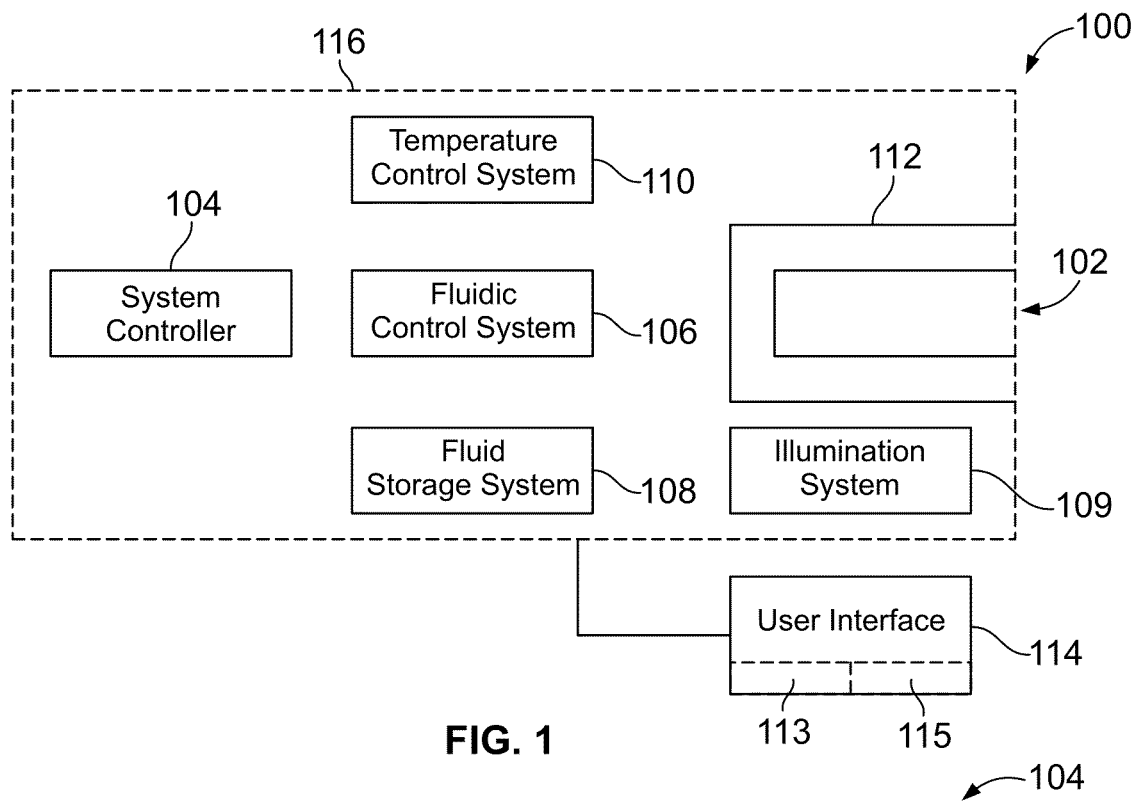
FIG. 1 is a block diagram of an exemplary system for biological or chemical analysis formed in accordance with one embodiment.

Embodiments described herein may be used in various biological or chemical processes and systems for academic or commercial analysis. More specifically, embodiments described herein may be used in various processes and systems where it is desired to detect an event, property, quality, or characteristic that is indicative of a designated reaction. For example, embodiments described herein include cartridges, biosensors, and their components as well as bioassay systems that operate with cartridges and biosensors. In particular embodiments, the cartridges and biosensors include a flow cell and one or more light sensors that are coupled together in a substantially unitary structure.

The bioassay systems may be configured to perform a plurality of designated reactions that may be detected individually or collectively. The biosensors and bioassay systems may be configured to perform numerous cycles in which the plurality of designated reactions occurs in parallel. For example, the bioassay systems may be used to sequence a dense array of DNA features through iterative cycles of enzymatic manipulation and image acquisition. As such, the cartridges and biosensors may include one or more microfluidic channels that deliver reagents or other reaction components to a reaction site. In some embodiments, the reaction sites are randomly distributed across a substantially planer surface. For example, the reaction sites may have an uneven distribution in which some reaction sites are located closer to each other than other reaction sites. In other embodiments, the reaction sites are patterned across a substantially planer surface in a predetermined manner. Each of the reaction sites may be associated with one or more light sensors that detect light from the associated reaction site. Yet in other embodiments, the reaction sites are located in reaction chambers that compartmentalize the designated reactions therein.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements whether or not they have that property.

As used herein, a "designated reaction" includes a change in at least one of a chemical, electrical, physical, or optical property (or quality) of an analyte-of-interest. In particular embodiments, the designated reaction is a positive binding event (e.g., incorporation of a fluorescently labeled biomolecule with the analyte-of-interest). More generally, the designated reaction may be a chemical transformation, chemical change, or chemical interaction. The designated reaction may also be a change in electrical properties. For example, the designated reaction may be a change in ion concentration within a solution. Exemplary reactions include, but are not limited to, chemical reactions such as reduction, oxidation, addition, elimination, rearrangement, esterification, amidation, etherification, cyclization, or substitution; binding interactions in which a first chemical binds to a second chemical; dissociation reactions in which two or more chemicals detach from each other; fluorescence; luminescence; bioluminescence; chemiluminescence; and biological reactions, such as nucleic acid replication, nucleic acid amplification, nucleic acid hybridization, nucleic acid ligation, phosphorylation, enzymatic catalysis, receptor binding, or ligand binding. The designated reaction can also be addition or elimination of a proton, for example, detectable as a change in pH of a surrounding solution or environment. An additional designated reaction can be detecting the flow of ions across a membrane (e.g., natural or synthetic bilayer membrane), for example as ions flow through a membrane the current is disrupted and the disruption can be detected.

In particular embodiments, the designated reaction includes the incorporation of a fluorescently-labeled molecule to an analyte. The analyte may be an oligonucleotide and the fluorescently-labeled molecule may be a nucleotide. The designated reaction may be detected when an excitation light is directed toward the oligonucleotide having the labeled nucleotide, and the fluorophore emits a detectable fluorescent signal. In alternative embodiments, the detected fluorescence is a result of chemiluminescence or bioluminescence. A designated reaction may also increase fluorescence (or Förster) resonance energy transfer (FRET), for example, by bringing a donor fluorophore in proximity to an acceptor fluorophore, decrease FRET by separating donor and acceptor fluorophores, increase fluorescence by separating a quencher from a fluorophore or decrease fluorescence by co-locating a quencher and fluorophore.

As used herein, a "reaction component" or "reactant" includes any substance that may be used to obtain a designated reaction. For example, reaction components include reagents, enzymes, samples, other biomolecules, and buffer solutions. The reaction components are typically delivered to a reaction site in a solution and/or immobilized at a reaction site. The reaction components may interact directly or indirectly with another substance, such as the analyte-of-interest.

As used herein, the term "reaction site" is a localized region where a designated reaction may occur. A reaction site may include support surfaces of a substrate where a substance may be immobilized thereon. For example, a reaction site may include a substantially planar surface in a channel of a flow cell that has a colony of nucleic acids thereon. Typically, but not always, the nucleic acids in the colony have the same sequence, being for example, clonal copies of a single stranded or double stranded template. However, in some embodiments a reaction site may contain only a single nucleic acid molecule, for example, in a single stranded or double stranded form. Furthermore, a plurality of reaction sites may be randomly distributed along the support surface or arranged in a predetermined manner (e.g., side-by-side in a matrix, such as in microarrays). A reaction site can also include a reaction chamber that at least partially defines a spatial region or volume configured to compartmentalize the designated reaction. As used herein, the term "reaction chamber" includes a spatial region that is in fluid communication with a flow channel. The reaction chamber may be at least partially separated from the surrounding environment or other spatial regions. For example, a plurality of reaction chambers may be separated from each other by shared walls. As a more specific example, the reaction chamber may include a cavity defined by interior surfaces of a well and have an opening or aperture so that the cavity may be in fluid communication with a flow channel. Biosensors including such reaction chambers are described in greater detail in international application no. PCT/US2011/057111, filed on Oct. 20, 2011, which is incorporated herein by reference in its entirety.

In some embodiments, the reaction chambers are sized and shaped relative to solids (including semi-solids) so that the solids may be inserted, fully or partially, therein. For example, the reaction chamber may be sized and shaped to accommodate only one capture bead. The capture bead may have clonally amplified DNA or other substances thereon. Alternatively, the reaction chamber may be sized and shaped to receive an approximate number of beads or solid substrates. As another example, the reaction chambers may also be filled with a porous gel or substance that is configured to control diffusion or filter fluids that may flow into the reaction chamber.

In some embodiments, light sensors (e.g., photodiodes) are associated with corresponding reaction sites. A light sensor that is associated with a reaction site is configured to detect light emissions from the associated reaction site when a designated reaction has occurred at the associated reaction site. In some cases, a plurality of light sensors (e.g. several pixels of a camera device) may be associated with a single reaction site. In other cases, a single light sensor (e.g. a single pixel) may be associated with a single reaction site or with a group of reaction sites. The light sensor, the reaction site, and other features of the biosensor may be configured so that at least some of the light is directly detected by the light sensor without being reflected.

As used herein, the term "adjacent" when used with respect to two reaction sites means no other reaction site is located between the two reaction sites. The term "adjacent" may have a similar meaning when used with respect to adjacent detection paths and adjacent light sensors (e.g., adjacent light sensors have no other light sensor therebetween). In some cases, a reaction site may not be adjacent to another reaction site, but may still be within an immediate vicinity of the other reaction site. A first reaction site may be in the immediate vicinity of a second reaction site when fluorescent emission signals from the first reaction site are detected by the light sensor associated with the second reaction site. More specifically, a first reaction site may be in the immediate vicinity of a second reaction site when the light sensor associated with the second reaction site detects, for example crosstalk from the first reaction site. Adjacent reaction sites can be contiguous such that they abut each other or the adjacent sites can be non-contiguous having an intervening space between.

As used herein, a "substance" includes items or solids, such as capture beads, as well as biological or chemical substances. As used herein, a "biological or chemical substance" includes biomolecules, samples-of-interest, analytes-of-interest, and other chemical compound(s). A biological or chemical substance may be used to detect, identify, or analyze other chemical compound(s), or function as intermediaries to study or analyze other chemical compound(s). In particular embodiments, the biological or chemical substances include a biomolecule. As used herein, a "biomolecule" includes at least one of a biopolymer, nucleoside, nucleic acid, polynucleotide, oligonucleotide, protein, enzyme, polypeptide, antibody, antigen, ligand, receptor, polysaccharide, carbohydrate, polyphosphate, cell, tissue, organism, or fragment thereof or any other biologically active chemical compound(s) such as analogs or mimetics of the aforementioned species.

In a further example, a biological or chemical substance or a biomolecule includes an enzyme or reagent used in a coupled reaction to detect the product of another reaction such as an enzyme or reagent used to detect pyrophosphate in a pyrosequencing reaction. Enzymes and reagents useful for pyrophosphate detection are described, for example, in U.S. Patent Publication No. 2005/0244870 A1, which is incorporated herein in its entirety.

Biomolecules, samples, and biological or chemical substances may be naturally occurring or synthetic and may be suspended in a solution or mixture within a spatial region. Biomolecules, samples, and biological or chemical substances may also be bound to a solid phase or gel material. Biomolecules, samples, and biological or chemical substances may also include a pharmaceutical composition. In some cases, biomolecules, samples, and biological or chemical substances of interest may be referred to as targets, probes, or analytes.

As used herein, a "biosensor" includes a structure having a plurality of reaction sites that is configured to detect designated reactions that occur at or proximate to the reaction sites. A biosensor may include a solid-state imaging device (e.g., CCD or CMOS imager) and, optionally, a flow cell mounted thereto. The flow cell may include at least one flow channel that is in fluid communication with the reaction sites. As one specific example, the biosensor is configured to fluidicly and electrically couple to a bioassay system. The bioassay system may deliver reactants to the reaction sites according to a predetermined protocol (e.g., sequencing-by-synthesis) and perform a plurality of imaging events. For example, the bioassay system may direct solutions to flow along the reaction sites. At least one of the solutions may include four types of nucleotides having the same or different fluorescent labels. The nucleotides may bind to corresponding oligonucleotides located at the reaction sites. The bioassay system may then illuminate the reaction sites using an excitation light source (e.g., solid-state light sources, such as light-emitting diodes or LEDs). The excitation light may have a predetermined wavelength or wavelengths, including a range of wavelengths. The excited fluorescent labels provide emission signals that may be detected by the light sensors.

In alternative embodiments, the biosensor may include electrodes or other types of sensors configured to detect other identifiable properties. For example, the sensors may be configured to detect a change in ion concentration. In another example, the sensors may be configured to detect the ion current flow across a membrane As used herein, a "cartridge" includes a structure that is configured to hold a biosensor. In some embodiments, the cartridge may include additional features, such as the light source (e.g., LEDs) that are configured to provide excitation light to the reactions sites of the biosensor. The cartridge may also include a fluidic storage system (e.g., storage for reagents, sample, and buffer) and a fluidic control system (e.g., pumps, valves, and the like) for fluidically transporting reaction components, sample, and the like to the reaction sites. For example, after the biosensor is prepared or manufactured, the biosensor may be coupled to a housing or container of the cartridge. In some embodiments, the biosensors and the cartridges may be self-contained, disposable units. However, other embodiments may include an assembly with removable parts that allow a user to access an interior of the biosensor or cartridge for maintenance or replacement of components or samples. The biosensor and the cartridge may be removably coupled or engaged to larger bioassay systems, such as a sequencing system, that conducts controlled reactions therein.

As used herein, when the terms "removably" and "coupled" (or "engaged") are used together to describe a relationship between the biosensor (or cartridge) and a system receptacle or interface of a bioassay system, the term is intended to mean that a connection between the biosensor (or cartridge) and the system receptacle is readily separable without destroying or damaging the system receptacle and/or the biosensor (or cartridge). Components are readily separable when the components may be separated from each other without undue effort or a significant amount of time spent in separating the components. For example, the biosensor (or cartridge) may be removably coupled or engaged to the system receptacle in an electrical manner such that the mating contacts of the bioassay system are not destroyed or damaged. The biosensor (or cartridge) may also be removably coupled or engaged to the system receptacle in a mechanical manner such that the features that hold the biosensor (or cartridge) are not destroyed or damaged. The biosensor (or cartridge) may also be removably coupled or engaged to the system receptacle in a fluidic manner such that the ports of the system receptacle are not destroyed or damaged. The system receptacle or a component is not considered to be destroyed or damaged if, for example, only a simple adjustment to the component (e.g., realignment) or a simple replacement (e.g., replacing a nozzle) is required.

As used herein, the term "fluid communication" or "fluidicly coupled" refers to two spatial regions being connected together such that a liquid or gas may flow between the two spatial regions. For example, a microfluidic channel may be in fluid communication with a reaction chamber such that a fluid may flow freely into the reaction chamber from the microfluidic channel. The terms "in fluid communication" or "fluidicly coupled" allow for two spatial regions being in fluid communication through one or more valves, restrictors, or other fluidic components that are configured to control or regulate a flow of fluid through a system.

As used herein, the term "immobilized," when used with respect to a biomolecule or biological or chemical substance, includes substantially attaching the biomolecule or biological or chemical substance at a molecular level to a surface. For example, a biomolecule or biological or chemical substance may be immobilized to a surface of the substrate material using adsorption techniques including non-covalent interactions (e.g., electrostatic forces, van der Waals, and dehydration of hydrophobic interfaces) and covalent binding techniques where functional groups or linkers facilitate attaching the biomolecules to the surface. Immobilizing biomolecules or biological or chemical substances to a surface of a substrate material may be based upon the properties of the substrate surface, the liquid medium carrying the biomolecule or biological or chemical substance, and the properties of the biomolecules or biological or chemical substances themselves. In some cases, a substrate surface may be functionalized (e.g., chemically or physically modified) to facilitate immobilizing the biomolecules (or biological or chemical substances) to the substrate surface. The substrate surface may be first modified to have functional groups bound to the surface. The functional groups may then bind to biomolecules or biological or chemical substances to immobilize them thereon. A substance can be immobilized to a surface via a gel, for example, as described in US Patent Publ. No. US 2011/0059865 A1, which is incorporated herein by reference.

In some embodiments, nucleic acids can be attached to a surface and amplified using bridge amplification. Useful bridge amplification methods are described, for example, in U.S. Pat. No. 5,641,658; WO 07/010251, U.S. Pat. No. 6,090,592; U.S. Patent Publ. No. 2002/0055100 A1; U.S. Pat. No. 7,115,400; U.S. Patent Publ. No. 2004/0096853 A1; U.S. Patent Publ. No. 2004/0002090 A1; U.S. Patent Publ. No. 2007/0128624 A1; and U.S. Patent Publ. No. 2008/0009420 A1, each of which is incorporated herein in its entirety. Another useful method for amplifying nucleic acids on a surface is rolling circle amplification (RCA), for example, using methods set forth in further detail below. In some embodiments, the nucleic acids can be attached to a surface and amplified using one or more primer pairs. For example, one of the primers can be in solution and the other primer can be immobilized on the surface (e.g., 5'-attached). By way of example, a nucleic acid molecule can hybridize to one of the primers on the surface followed by extension of the immobilized primer to produce a first copy of the nucleic acid. The primer in solution then hybridizes to the first copy of the nucleic acid which can be extended using the first copy of the nucleic acid as a template. Optionally, after the first copy of the nucleic acid is produced, the original nucleic acid molecule can hybridize to a second immobilized primer on the surface and can be extended at the same time or after the primer in solution is extended. In any embodiment, repeated rounds of extension (e.g., amplification) using the immobilized primer and primer in solution provide multiple copies of the nucleic acid.

In particular embodiments, the assay protocols executed by the systems and methods described herein include the use of natural nucleotides and also enzymes that are configured to interact with the natural nucleotides. Natural nucleotides include, for example, ribonucleotides or deoxyribonucleotides. Natural nucleotides can be in the mono-, di-, or tri-phosphate form and can have a base selected from adenine (A), Thymine (T), uracil (U), guanine (G) or cytosine (C). It will be understood however that non-natural nucleotides, modified nucleotides or analogs of the aforementioned nucleotides can be used. Some examples of useful non-natural nucleotides are set forth below in regard to reversible terminator-based sequencing by synthesis methods.

In embodiments that include reaction chambers, items or solid substances (including semi-solid substances) may be disposed within the reaction chambers. When disposed, the item or solid may be physically held or immobilized within the reaction chamber through an interference fit, adhesion, or entrapment. Exemplary items or solids that may be disposed within the reaction chambers include polymer beads, pellets, agarose gel, powders, quantum dots, or other solids that may be compressed and/or held within the reaction chamber. In particular embodiments, a nucleic acid superstructure, such as a DNA ball, can be disposed in or at a reaction chamber, for example, by attachment to an interior surface of the reaction chamber or by residence in a liquid within the reaction chamber. A DNA ball or other nucleic acid superstructure can be preformed and then disposed in or at the reaction chamber. Alternatively, a DNA ball can be synthesized in situ at the reaction chamber. A DNA ball can be synthesized by rolling circle amplification to produce a concatamer of a particular nucleic acid sequence and the concatamer can be treated with conditions that form a relatively compact ball. DNA balls and methods for their synthesis are described, for example in, U.S. Patent Publ. Nos. 2008/0242560 A1 or 2008/0234136 A1, each of which is incorporated herein in its entirety. A substance that is held or disposed in a reaction chamber can be in a solid, liquid, or gaseous state.

FIG. 1 is a block diagram of an exemplary bioassay system 100 for biological or chemical analysis formed in accordance with one embodiment. The term "bioassay" is not intended to be limiting as the bioassay system 100 may operate to obtain any information or data that relates to at least one of a biological or chemical substance. In some embodiments, the bioassay system 100 is a workstation that may be similar to a bench-top device or desktop computer. For example, a majority (or all) of the systems and components for conducting the designated reactions can be within a common housing 116.

In particular embodiments, the bioassay system 100 is a nucleic acid sequencing system (or sequencer) configured for various applications, including but not limited to de novo sequencing, resequencing of whole genomes or target genomic regions, and metagenomics. The sequencer may also be used for DNA or RNA analysis. In some embodiments, the bioassay system 100 may also be configured to generate reaction sites in a biosensor. For example, the bioassay system 100 may be configured to receive a sample and generate surface attached clusters of clonally amplified nucleic acids derived from the sample. Each cluster may constitute or be part of a reaction site in the biosensor.

The exemplary bioassay system 100 may include a system receptacle or interface 112 that is configured to interact with a biosensor 102 to perform designated reactions within the biosensor 102. In the following description with respect to FIG. 1, the biosensor 102 is loaded into the system receptacle 112. However, it is understood that a cartridge that includes the biosensor 102 may be inserted into the system receptacle 112 and in some states the cartridge can be removed temporarily or permanently. As described above, the cartridge may include, among other things, fluidic control and fluidic storage components.

In particular embodiments, the bioassay system 100 is configured to perform a large number of parallel reactions within the biosensor 102. The biosensor 102 includes one or more reaction sites where designated reactions can occur.

The reaction sites may be, for example, immobilized to a solid surface of the biosensor or immobilized to beads (or other movable substrates) that are located within corresponding reaction chambers of the biosensor. The reaction sites can include, for example, clusters of clonally amplified nucleic acids. The biosensor 102 may include a solid-state imaging device (e.g., CCD or CMOS imager) and a flow cell mounted thereto. The flow cell may include one or more flow channels that receive a solution from the bioassay system 100 and direct the solution toward the reaction sites. Optionally, the biosensor 102 can be configured to engage a thermal element for transferring thermal energy into or out of the flow channel.

The bioassay system 100 may include various components, assemblies, and systems (or sub-systems) that interact with each other to perform a predetermined method or assay protocol for biological or chemical analysis. For example, the bioassay system 100 includes a system controller 104 that may communicate with the various components, assemblies, and sub-systems of the bioassay system 100 and also the biosensor 102. For example, in addition to the system receptacle 112, the bioassay system 100 may also include a fluidic control system 106 to control the flow of fluid throughout a fluid network of the bioassay system 100 and the biosensor 102; a fluid storage system 108 that is configured to hold all fluids (e.g., gas or liquids) that may be used by the bioassay system; a temperature control system 110 that may regulate the temperature of the fluid in the fluid network, the fluid storage system 108, and/or the biosensor 102; and an illumination system 111 that is configured to illuminate the biosensor 102. As described above, if a cartridge having the biosensor 102 is loaded into the system receptacle 112, the cartridge may also include fluidic control and fluidic storage components.

Also shown, the bioassay system 100 may include a user interface 114 that interacts with the user. For example, the user interface 114 may include a display 113 to display or request information from a user and a user input device 115 to receive user inputs. In some embodiments, the display 113 and the user input device 115 are the same device. For example, the user interface 114 may include a touch-sensitive display configured to detect the presence of an individual's touch and also identify a location of the touch on the display. However, other user input devices 115 may be used, such as a mouse, touchpad, keyboard, keypad, handheld scanner, voice-recognition system, motion-recognition system, and the like. As will be discussed in greater detail below, the bioassay system 100 may communicate with various components, including the biosensor 102 (e.g. in the form of a cartridge), to perform the designated reactions. The bioassay system 100 may also be configured to analyze data obtained from the biosensor to provide a user with desired information.

The system controller 104 may include any processor-based or microprocessor-based system, including systems using microcontrollers, reduced instruction set computers (RISC), application specific integrated circuits (ASICs), field programmable gate array (FPGAs), logic circuits, and any other circuit or processor capable of executing functions described herein. The above examples are exemplary only, and are thus not intended to limit in any way the definition and/or meaning of the term system controller. In the exemplary embodiment, the system controller 104 executes a set of instructions that are stored in one or more storage elements, memories, or modules in order to at least one of obtain and analyze detection data. Storage elements may be in the form of information sources or physical memory elements within the bioassay system 100.

The set of instructions may include various commands that instruct the bioassay system 100 or biosensor 102 to perform specific operations such as the methods and processes of the various embodiments described herein. The set of instructions may be in the form of a software program, which may form part of a tangible, non-transitory computer readable medium or media. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

The software may be in various forms such as system software or application software. Further, the software may be in the form of a collection of separate programs, or a program module within a larger program or a portion of a program module. The software also may include modular programming in the form of object-oriented programming. After obtaining the detection data, the detection data may be automatically processed by the bioassay system 100, processed in response to user inputs, or processed in response to a request made by another processing machine (e.g., a remote request through a communication link).

The system controller 104 may be connected to the biosensor 102 and the other components of the bioassay system 100 via communication links. The system controller 104 may also be communicatively connected to off-site systems or servers. The communication links may be hardwired or wireless. The system controller 104 may receive user inputs or commands, from the user interface 114 and the user input device 115.

The fluidic control system 106 includes a fluid network and is configured to direct and regulate the flow of one or more fluids through the fluid network. The fluid network may be in fluid communication with the biosensor 102 and the fluid storage system 108. For example, select fluids may be drawn from the fluid storage system 108 and directed to the biosensor 102 in a controlled manner, or the fluids may be drawn from the biosensor 102 and directed toward, for example, a waste reservoir in the fluid storage system 108. Although not shown, the fluidic control system 106 may include flow sensors that detect a flow rate or pressure of the fluids within the fluid network. The sensors may communicate with the system controller 104.

The temperature control system 110 is configured to regulate the temperature of fluids at different regions of the fluid network, the fluid storage system 108, and/or the biosensor 102. For example, the temperature control system 110 may include a thermocycler that interfaces with the biosensor 102 and controls the temperature of the fluid that flows along the reaction sites in the biosensor 102. The temperature control system 110 may also regulate the temperature of solid elements or components of the bioassay system 100 or the biosensor 102. Although not shown, the temperature control system 110 may include sensors to detect the temperature of the fluid or other components. The sensors may communicate with the system controller 104.

The fluid storage system 108 is in fluid communication with the biosensor 102 and may store various reaction components or reactants that are used to conduct the designated reactions therein. The fluid storage system 108 may also store fluids for washing or cleaning the fluid network and biosensor 102 and for diluting the reactants. For example, the fluid storage system 108 may include various reservoirs to store samples, reagents, enzymes, other biomolecules, buffer solutions, aqueous, and non-polar solutions, and the like. Furthermore, the fluid storage system 108 may also include waste reservoirs for receiving waste products from the biosensor 102. In embodiments that include a cartridge, the cartridge may include one or more of a fluid storage system, fluidic control system or temperature control system. Accordingly, one or more of the components set forth herein as relating to those systems can be contained within a cartridge housing. For example, a cartridge can have various reservoirs to store samples, reagents, enzymes, other biomolecules, buffer solutions, aqueous, and non-polar solutions, waste, and the like. As such, one or more of a fluid storage system, fluidic control system or temperature control system can be removably engaged with a bioassay system via a cartridge or other biosensor.

The illumination system 111 may include a light source (e.g., one or more LEDs) and a plurality of optical components to illuminate the biosensor. Examples of light sources may include lasers, arc lamps, LEDs, or laser diodes. The optical components may be, for example, reflectors, dichroics, beam splitters, collimators, lenses, filters, wedges, prisms, mirrors, detectors, and the like. In embodiments that use an illumination system, the illumination system 111 may be configured to direct an excitation light to reaction sites. As one example, fluorophores may be excited by green wavelengths of light, as such the wavelength of the excitation light may be approximately 532 nm.

The system receptacle or interface 112 is configured to engage the biosensor 102 in at least one of a mechanical, electrical, and fluidic manner. The system receptacle 112 may hold the biosensor 102 in a desired orientation to facilitate the flow of fluid through the biosensor 102. The system receptacle 112 may also include electrical contacts that are configured to engage the biosensor 102 so that the bioassay system 100 may communicate with the biosensor 102 and/or provide power to the biosensor 102. Furthermore, the system receptacle 112 may include fluidic ports (e.g., nozzles) that are configured to engage the biosensor 102. In some embodiments, the biosensor 102 is removably coupled to the system receptacle 112 in a mechanical manner, in an electrical manner, and also in a fluidic manner.

In addition, the bioassay system 100 may communicate remotely with other systems or networks or with other bioassay systems 100. Detection data obtained by the bioassay system(s) 100 may be stored in a remote database.

Figure 2:
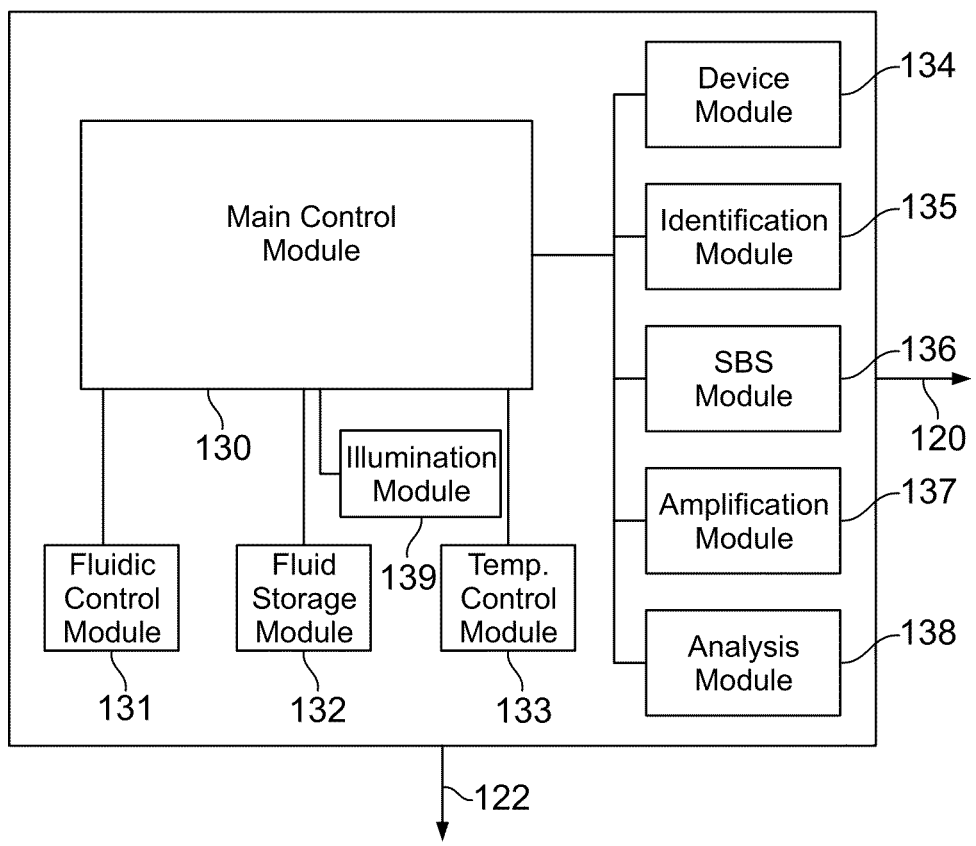
FIG. 2 is a block diagram of an exemplary system controller that may be used in the system of FIG. 1.

FIG. 2 is a block diagram of the system controller 104 in the exemplary embodiment. In one embodiment, the system controller 104 includes one or more processors or modules that can communicate with one another. Each of the processors or modules may include an algorithm (e.g., instructions stored on a tangible and/or non-transitory computer readable storage medium) or sub-algorithms to perform particular processes. The system controller 104 is illustrated conceptually as a collection of modules, but may be implemented utilizing any combination of dedicated hardware boards, DSPs, processors, etc. Alternatively, the system controller 104 may be implemented utilizing an off-the-shelf PC with a single processor or multiple processors, with the functional operations distributed between the processors. As a further option, the modules described below may be implemented utilizing a hybrid configuration in which certain modular functions are performed utilizing dedicated hardware, while the remaining modular functions are performed utilizing an off-the-shelf PC and the like. The modules also may be implemented as software modules within a processing unit.

During operation, a communication link 120 may transmit information (e.g. commands) to or receive information (e.g. data) from the biosensor 102 (FIG. 1) and/or the sub-systems 106, 108, 110 (FIG. 1). A communication link 122 may receive user input from the user interface 114 (FIG. 1) and transmit data or information to the user interface 114. Data from the biosensor 102 or sub-systems 106, 108, 110 may be processed by the system controller 104 in real-time during a bioassay session. Additionally or alternatively, data may be stored temporarily in a system memory during a bioassay session and processed in slower than real-time or off-line operation.

As shown in FIG. 2, the system controller 104 may include a plurality of modules 131-139 that communicate with a main control module 130. The main control module 130 may communicate with the user interface 114 (FIG. 1). Although the modules 131-139 are shown as communicating directly with the main control module 130, the modules 131-139 may also communicate directly with each other, the user interface 114, and the biosensor 102. Also, the modules 131-139 may communicate with the main control module 130 through the other modules.

The plurality of modules 131-139 include system modules 131-133, 139 that communicate with the sub-systems 106, 108, 110, and 111, respectively. The fluidic control module 131 may communicate with the fluidic control system 106 to control the valves and flow sensors of the fluid network for controlling the flow of one or more fluids through the fluid network. The fluid storage module 132 may notify the user when fluids are low or when the waste reservoir is at or near capacity. The fluid storage module 132 may also communicate with the temperature control module 133 so that the fluids may be stored at a desired temperature. The illumination module 139 may communicate with the illumination system 109 to illuminate the reaction sites at designated times during a protocol, such as after the designated reactions (e.g., binding events) have occurred.

The plurality of modules 131-139 may also include a device module 134 that communicates with the biosensor 102 and an identification module 135 that determines identification information relating to the biosensor 102. The device module 134 may, for example, communicate with the system receptacle 112 to confirm that the biosensor has established an electrical and fluidic connection with the bioassay system 100. The identification module 135 may receive signals that identify the biosensor 102. The identification module 135 may use the identity of the biosensor 102 to provide other information to the user. For example, the identification module 135 may determine and then display a lot number, a date of manufacture, or a protocol that is recommended to be run with the biosensor 102.

The plurality of modules 131-139 may also include a detection data analysis module 138 that receives and analyzes the signal data (e.g., image data) from the biosensor 102. The signal data may be stored for subsequent analysis or may be transmitted to the user interface 114 to display desired information to the user. In some embodiments, the signal data may be processed by the solid-state imager (e.g., CMOS image sensor) before the detection data analysis module 138 receives the signal data.

Protocol modules 136 and 137 communicate with the main control module 130 to control the operation of the sub-systems 106, 108, and 110 when conducting predetermined assay protocols. The protocol modules 136 and 137 may include sets of instructions for instructing the bioassay system 100 to perform specific operations pursuant to predetermined protocols. As shown, the protocol module may be a sequencing-by-synthesis (SBS) module 136 that is configured to issue various commands for performing sequencing-by-synthesis processes. In SBS, extension of a nucleic acid primer along a nucleic acid template is monitored to determine the sequence of nucleotides in the template. The underlying chemical process can be polymerization (e.g. as catalyzed by a polymerase enzyme) or ligation (e.g. catalyzed by a ligase enzyme). In a particular polymerase-based SBS embodiment, fluorescently labeled nucleotides are added to a primer (thereby extending the primer) in a template dependent fashion such that detection of the order and type of nucleotides added to the primer can be used to determine the sequence of the template. For example, to initiate a first SBS cycle, commands can be given to deliver one or more labeled nucleotides, DNA polymerase, etc., into/through a flow cell that houses an array of nucleic acid templates. The nucleic acid templates may be located at corresponding reaction sites. Those reaction sites where primer extension causes a labeled nucleotide to be incorporated can be detected through an imaging event. During an imaging event, the illumination system 111 may provide an excitation light to the reaction sites. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination a command can be given to deliver a deblocking reagent to the flow cell (before or after detection occurs). One or more commands can be given to effect wash(es) between the various delivery steps. The cycle can then be repeated n times to extend the primer by n nucleotides, thereby detecting a sequence of length n. Exemplary sequencing techniques are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

For the nucleotide delivery step of an SBS cycle, either a single type of nucleotide can be delivered at a time, or multiple different nucleotide types (e.g. A, C, T and G together) can be delivered. For a nucleotide delivery configuration where only a single type of nucleotide is present at a time, the different nucleotides need not have distinct labels since they can be distinguished based on temporal separation inherent in the individualized delivery. Accordingly, a sequencing method or apparatus can use single color detection. For example, an excitation source need only provide excitation at a single wavelength or in a single range of wavelengths. For a nucleotide delivery configuration where delivery results in multiple different nucleotides being present in the flow cell at one time, sites that incorporate different nucleotide types can be distinguished based on different fluorescent labels that are attached to respective nucleotide types in the mixture. For example, four different nucleotides can be used, each having one of four different fluorophores. In one embodiment, the four different fluorophores can be distinguished using excitation in four different regions of the spectrum. For example, four different excitation radiation sources can be used. Alternatively, fewer than four different excitation sources can be used, but optical filtration of the excitation radiation from a single source can be used to produce different ranges of excitation radiation at the flow cell.

In some embodiments, fewer than four different colors can be detected in a mixture having four different nucleotides. For example, pairs of nucleotides can be detected at the same wavelength, but distinguished based on a difference in intensity for one member of the pair compared to the other, or based on a change to one member of the pair (e.g. via chemical modification, photochemical modification or physical modification) that causes apparent signal to appear or disappear compared to the signal detected for the other member of the pair. Exemplary apparatus and methods for distinguishing four different nucleotides using detection of fewer than four colors are described for example in U.S. Pat. App. Ser. Nos. 61/538,294 and 61/619,878, which are incorporated herein by reference their entireties. U.S. application Ser. No. 13/624,200, which was filed on Sep. 21, 2012, is also incorporated by reference in its entirety.

The plurality of protocol modules may also include a sample-preparation (or generation) module 137 that is configured to issue commands to the fluidic control system 106 and the temperature control system 110 for amplifying a product within the biosensor 102. For example, the biosensor 102 may be engaged to the bioassay system 100. The amplification module 137 may issue instructions to the fluidic control system 106 to deliver necessary amplification components to reaction chambers within the biosensor 102. In other embodiments, the reaction sites may already contain some components for amplification, such as the template DNA and/or primers. After delivering the amplification components to the reaction chambers, the amplification module 137 may instruct the temperature control system 110 to cycle through different temperature stages according to known amplification protocols. In some embodiments, the amplification and/or nucleotide incorporation is performed isothermally.

The SBS module 136 may issue commands to perform bridge PCR where clusters of clonal amplicons are formed on localized areas within a channel of a flow cell. After generating the amplicons through bridge PCR, the amplicons may be "linearized" to make single stranded template DNA, or sstDNA, and a sequencing primer may be hybridized to a universal sequence that flanks a region of interest. For example, a reversible terminator-based sequencing by synthesis method can be used as set forth above or as follows.

Each sequencing cycle can extend a sstDNA by a single base which can be accomplished for example by using a modified DNA polymerase and a mixture of four types of nucleotides. The different types of nucleotides can have unique fluorescent labels, and each nucleotide can further have a reversible terminator that allows only a single-base incorporation to occur in each cycle. After a single base is added to the sstDNA, excitation light may be incident upon the reaction sites and fluorescent emissions may be detected. After detection, the fluorescent label and the terminator may be chemically cleaved from the sstDNA. Another similar sequencing cycle may follow. In such a sequencing protocol, the SBS module 136 may instruct the fluidic control system 106 to direct a flow of reagent and enzyme solutions through the biosensor 102. Exemplary reversible terminator-based SBS methods which can be utilized with the apparatus and methods set forth herein are described in US Patent Application Publication No. 2007/0166705 A1, US Patent Application Publication No. 2006/0188901 A1, U.S. Pat. No. 7,057,026, US Patent Application Publication No. 2006/

0240439 A1, US Patent Application Publication No. 2006/ 0281109 A1, PCT Publication No. WO 05/065814, US Patent Application Publication No. 2005/0100900 A1, PCT Publication No. WO 06/064199 and PCT Publication No. WO 07/010251, each of which is incorporated herein by reference in its entirety. Exemplary reagents for reversible terminator-based SBS are described in U.S. Pat. Nos. 7,541, 444; 7,057,026; 7,414,116; 7,427,673; 7,566,537; 7,592,435 and WO 07/135368, each of which is incorporated herein by reference in its entirety.

In some embodiments, the amplification and SBS modules may operate in a single assay protocol where, for example, template nucleic acid is amplified and subsequently sequenced within the same cartridge.

The bioassay system 100 may also allow the user to reconfigure an assay protocol. For example, the bioassay system 100 may offer options to the user through the user interface 114 for modifying the determined protocol. For example, if it is determined that the biosensor 102 is to be used for amplification, the bioassay system 100 may request a temperature for the annealing cycle. Furthermore, the bioassay system 100 may issue warnings to a user if a user has provided user inputs that are generally not acceptable for the selected assay protocol.

Figure 3:
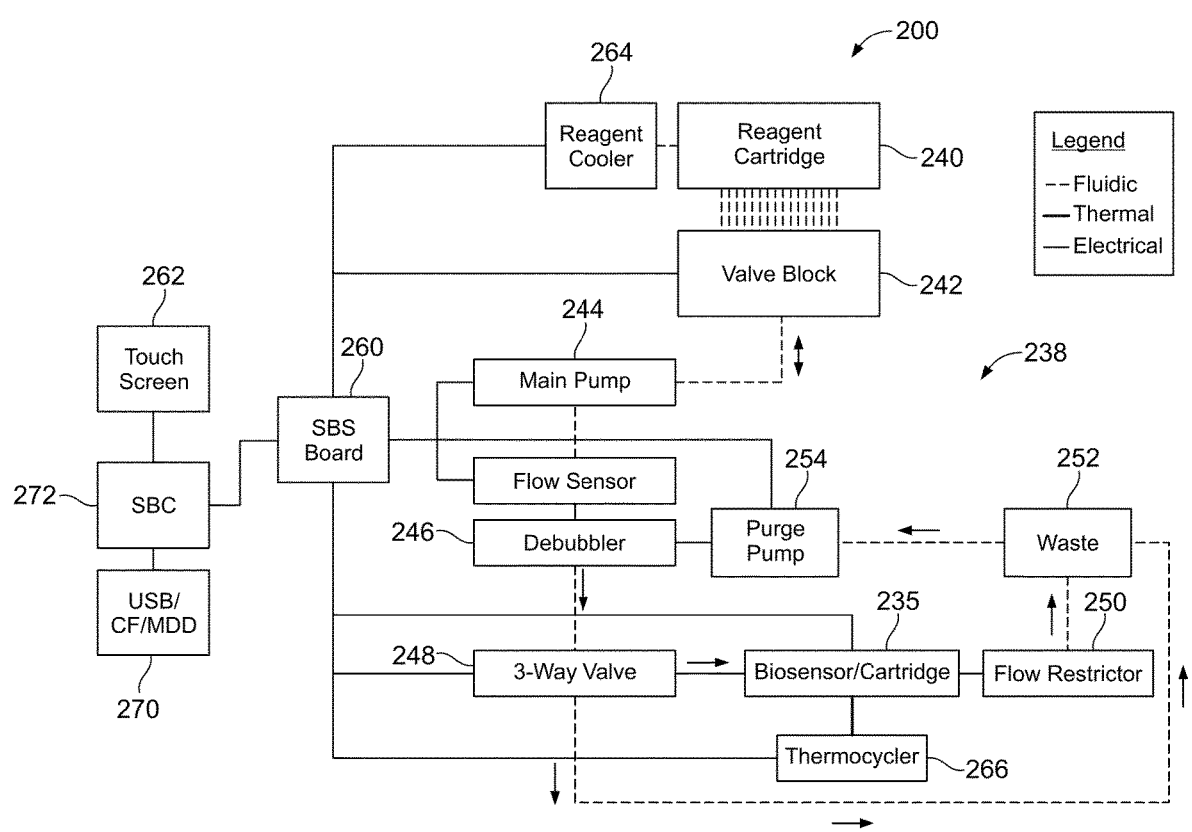
FIG. 3 is a block diagram of an exemplary workstation for biological or chemical analysis in accordance with one embodiment.

FIG. 3 is a block diagram of an exemplary workstation 200 for biological or chemical analysis in accordance with one embodiment. The workstation 200 may have similar features, systems, and assemblies as the bioassay system 100 described above. For example, the workstation 200 may have a fluidic control system, such as the fluidic control system 106 (FIG. 1), that is fluidicly coupled to a biosensor (or cartridge) 235 through a fluid network 238. The fluid network 238 may include a reagent cartridge 240, a valve block 242, a main pump 244, a debubbler 246, a 3-way valve 248, a flow restrictor 250, a waste removal system 252, and a purge pump 254. In particular embodiments, most of the components or all of the components described above are within a common workstation housing (not shown). Although not shown, the workstation 200 may also include an illumination system, such as the illumination system 111, that is configured to provide an excitation light to the reaction sites.

A flow of fluid is indicated by arrows along the fluid network 238. For example, reagent solutions may be removed from the reagent cartridge 240 and flow through the valve block 242. The valve block 242 may facilitate creating a zero-dead volume of the fluid flowing to the cartridge 235 from the reagent cartridge 240. The valve block 242 can select or permit one or more liquids within the reagent cartridge 240 to flow through the fluid network 238. For example, the valve block 242 can include solenoid valves that have a compact arrangement. Each solenoid valve can control the flow of a fluid from a single reservoir bag. In some embodiments, the valve block 242 can permit two or more different liquids to flow into the fluid network 238 at the same time thereby mixing the two or more different liquids. After leaving the valve block 242, the fluid may flow through the main pump 244 and to the debubbler 246. The debubbler 246 is configured to remove unwanted gases that have entered or been generated within the fluid network 238.

From the debubbler 246, fluid may flow to the 3-way valve 248 where the fluid is either directed to the cartridge 235 or bypassed to the waste removal system 252. A flow of the fluid within the cartridge 235 may be at least partially controlled by the flow restrictor 250 located downstream from the cartridge 235. Furthermore, the flow restrictor 250 and the main pump 244 may coordinate with each other to control the flow of fluid across reaction sites and/or control the pressure within the fluid network 238. Fluid may flow through the cartridge 235 and onto the waste removal system 252. Optionally, fluid may flow through the purge pump 254 and into, for example, a waste reservoir bag within the reagent cartridge 240.

Also shown in FIG. 3, the workstation 200 may include a temperature control system, such as the temperature control system 110, that is configured to regulate or control a thermal environment of the different components and subsystems of the workstation 200. The temperature control system 110 can include a reagent cooler 264 that is configured to control the temperature requirements of various fluids used by the workstation 200, and a thermocycler 266 that is configured to control the temperature of a cartridge 235. The thermocycler 266 can include a thermal element (not shown) that interfaces with the cartridge.

Furthermore, the workstation 200 may include a system controller or SBS board 260 that may have similar features as the system controller 104 described above. The SBS board 260 may communicate with the various components and sub-systems of the workstation 200 as well as the cartridge 235. Furthermore, the SBS board 260 may communicate with remote systems to, for example, store data or receive commands from the remote systems. The workstation 200 may also include a touch screen user interface 262 that is operatively coupled to the SBS board 260 through a single-board computer (SBC) 272. The workstation 200 may also include one or more user accessible data communication ports and/or drives. For example a workstation 200 may include one or more universal serial bus (USB) connections for computer peripherals, such as a flash or jump drive, a compact-flash (CF) drive and/or a hard drive 270 for storing user data in addition to other software.

Figure 4:
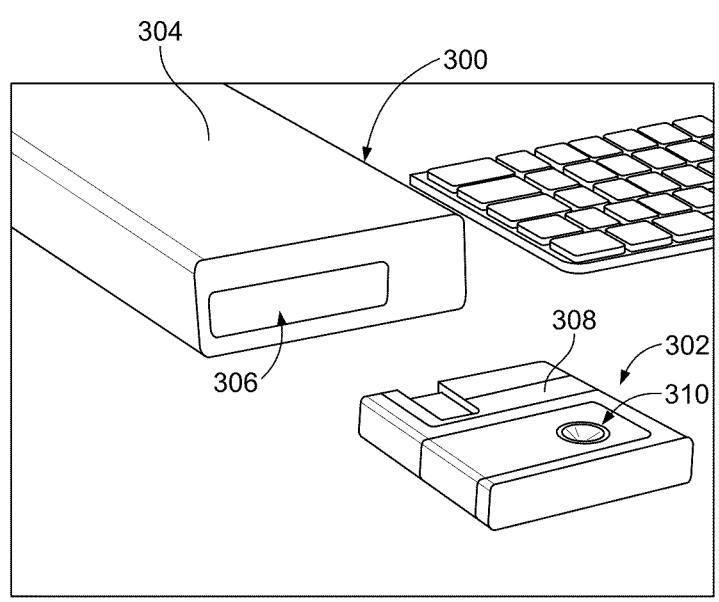
FIG. 4 is a perspective view of an exemplary workstation and an exemplary cartridge in accordance with one embodiment.

FIG. 4 is a perspective view of a workstation 300 and a cartridge 302 that may include one or more biosensors (not shown) as described herein. The workstation 300 may include similar components as described above with respect to the bioassay system 100 and the workstation 200 and may operate in a similar manner. For example, the workstation 300 may include a workstation housing 304 and a system receptacle 306 that is configured to receive and engage the cartridge 302. The system receptacle may at least one of fluidically or electrically engage the cartridge 302. The workstation housing 304 may hold, for example, a system controller, a fluid storage system, a fluidic control system, and a temperature control system as described above. In FIG. 4, the workstation 300 does not include a user interface or display that is coupled to the workstation housing 304. However, a user interface may be communicatively coupled to the housing 304 (and the components/systems therein) through a communication link. Thus, the user interface and the workstation 300 may be remotely located with respect to each other. Together, the user interface and the workstation 300 (or a plurality of workstations) may constitute a bioassay system.

As shown, the cartridge 302 includes a cartridge housing 308 having at least one port 310 that provides access to an interior of the cartridge housing 308. For example, a solution that is configured to be used in the cartridge 302 during the controlled reactions may be inserted through the port 310 by a technician or by the workstation 300. The system receptacle 306 and the cartridge 302 may be sized and shaped relative to each other such that the cartridge 302 may be inserted into a receptacle cavity (not shown) of the system receptacle 306.

Figure 5:
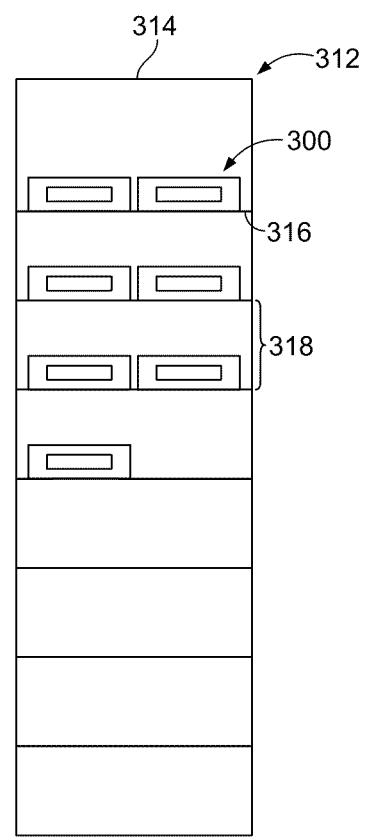
FIG. 5 is a front view of an exemplary rack assembly that includes a plurality of the workstations of FIG. 4.

FIG. 5 is a front view of a rack assembly 312 having a cabinet or carriage 314 with a plurality of the workstations 300 loaded thereon. The cabinet 314 may include one or more shelves 316 that define one or more reception spaces 318 configured to receive one or more workstations 300. Although not shown, the workstations 300 may be communicatively coupled to a communication network that permits a user to control operation of the workstations 300. In some embodiments, a bioassay system includes a plurality of workstations, such as the workstations 300, and a single user interface configured to control operation of the multiple workstations.

Figure 6:
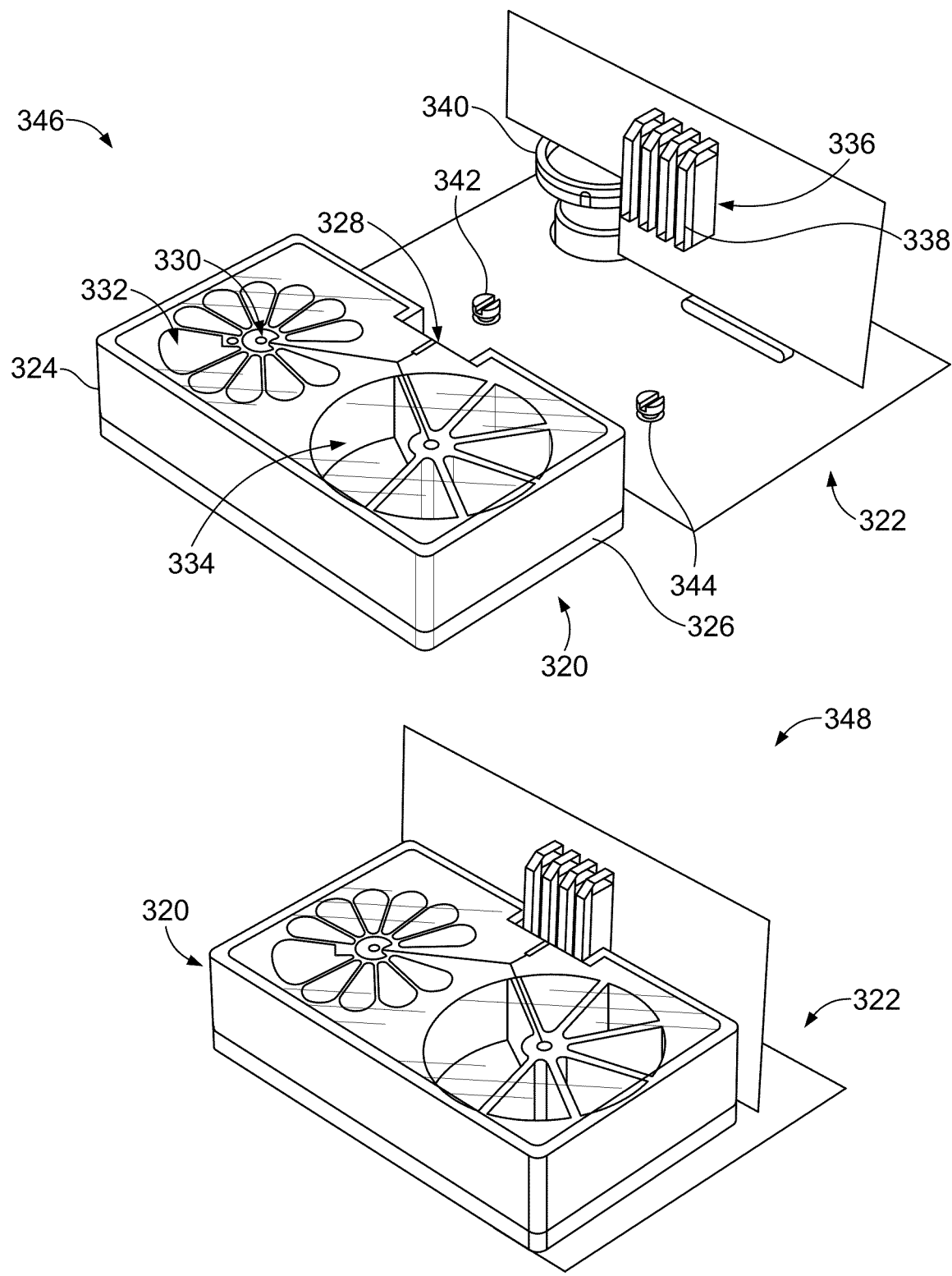
FIG. 6 illustrates internal components of an exemplary cartridge.

FIG. 6 illustrates various features of the cartridge 302 (FIG. 4) in accordance with one embodiment. As shown, the cartridge 302 may include a sample assembly 320, and the system receptacle 306 may include a light assembly 322. Stage 346 shown in FIG. 6 represents the spatial relationship between the first and second sub-assemblies 320 and 322 when they are separate from each other. At stage 348, the first and second sub-assemblies 320 and 322 are joined together. The cartridge housing 308 (FIG. 4) may enclose the joined first and second sub-assemblies 320 and 322.

In the illustrated embodiment, the first sub-assembly 320 includes a base 326 and a reaction-component body 324 that is mounted onto the base 326. Although not shown, one or more biosensors may be mounted to the base 326 in a recess 328 that is defined, at least in part, by the reaction-component body 324 and the base 326. For example, at least four biosensors may be mounted to the base 326. In some embodiments, the base 326 is a printed circuit board having circuitry that enables communication between the different components of the cartridge and the workstation 300 (FIG. 4). For example, the reaction-component body 324 may include a rotary valve 330 and reagent reservoirs 332 that are fluidically coupled to the rotary valve 330. The reaction-component body 324 may also include additional reservoirs 334.

The second sub-assembly 322 includes a light assembly 336 that includes a plurality of light directing channels 338. Each light directing channel 338 is optically coupled to a light source (not shown), such as a light-emitting diode (LED). The light source(s) are configured to provide an excitation light that is directed by the light directing channels 338 onto the biosensors. In alternative embodiments, the cartridge may not include a light source(s). In such embodiments, the light source(s) may be located in the workstation 300. When the cartridge is inserted into the system receptacle 306 (FIG. 4), the cartridge 302 may align with the light source(s) so that the biosensors may be illuminated.

Also shown in FIG. 6, the second sub-assembly 322 includes a cartridge pump 340 that is fluidically coupled to ports 342 and 344. When the first and second sub-assemblies 320 and 322 are joined together, the port 342 is coupled to the rotary valve 330 and the port 344 is coupled to the other reservoirs 334. The cartridge pump 340 may be activated to direct reaction components from the reservoirs 332 and/or 334 to the biosensors according to a designated protocol.

Figure 7:
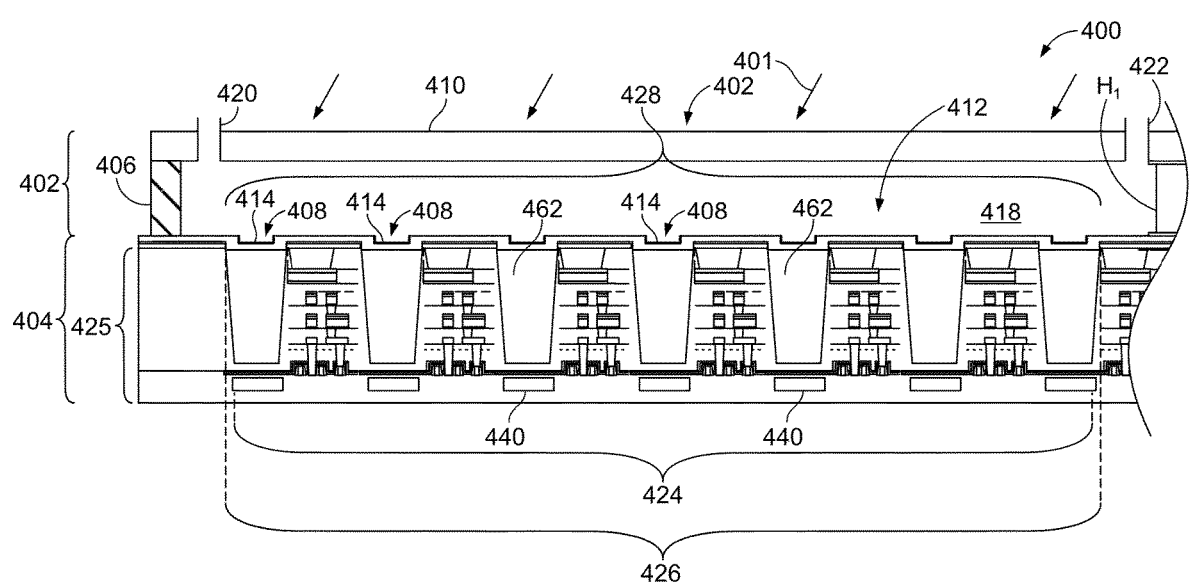
FIG. 7 illustrates a cross-section of a biosensor formed in accordance with one embodiment.

FIG. 7 illustrates a cross-section of a portion of an exemplary biosensor 400 formed in accordance with one embodiment. The biosensor 400 may include similar features as the biosensor 102 (FIG. 1) described above and may be used in, for example, the cartridge 302 (FIG. 4). As shown, the biosensor 400 may include a flow cell 402 that is coupled directly or indirectly to a detection device 404. The flow cell 402 may be mounted to the detection device 404. In the illustrated embodiment, the flow cell 402 is affixed directly to the detection device 404 through one or more securing mechanisms (e.g., adhesive, bond, fasteners, and the like). In some embodiments, the flow cell 402 may be removably coupled to the detection device 404.

In the illustrated embodiment, the detection device 404 includes a device base 425. In particular embodiments, the device base 425 includes a plurality of stacked layers (e.g., silicon layer, dielectric layer, metal-dielectric layers, etc.). The device base 425 may include a sensor array 424 of light sensors 440, a guide array 426 of light guides 462, and a reaction array 428 of reaction recesses 408 that have corresponding reaction sites 414. In certain embodiments, the components are arranged such that each light sensor 440 aligns with a single light guide 462 and a single reaction site 414. However, in other embodiments, a single light sensor 440 may receive photons through more than one light guide 462 and/or from more than one reaction site 414. As used herein, a single light sensor may include one pixel or more than one pixel.

Moreover, it is noted that the term "array" or "sub-array" does not necessarily include each and every item of a certain type that the detection device may have. For example, the sensor array 424 may not include each and every light sensor in the detection device 404. Instead, the detection device 404 may include other light sensors (e.g., other array(s) of light sensors). As another example, the guide array 426 may not include each and every light guide of the detection device. Instead, there may be other light guides that are configured differently than the light guides 462 or that have different relationships with other elements of the detection device 404. As such, unless explicitly recited otherwise, the term "array" may or may not include all such items of the detection device.

In the illustrated embodiment, the flow cell 402 includes a sidewall 406 and a flow cover 410 that is supported by the sidewall 406 and other sidewalls (not shown). The sidewalls are coupled to the detector surface 412 and extend between the flow cover 410 and the detector surface 412. In some embodiments, the sidewalls are formed from a curable adhesive layer that bonds the flow cover 410 to the detection device 404.

The flow cell 402 is sized and shaped so that a flow channel 418 exists between the flow cover 410 and the detection device 404. As shown, the flow channel 418 may include a height $H_1$. By way of example only, the height $H_1$ may be between about 50-400 μm (microns) or, more particularly, about 80-200 μm. In the illustrated embodiment, the height $H_1$ is about 100 μm. The flow cover 410 may include a material that is transparent to excitation light 401 propagating from an exterior of the biosensor 400 into the flow channel 418. As shown in FIG. 7, the excitation light 401 approaches the flow cover 410 at a non-orthogonal angle. However, this is only for illustrative purposes as the excitation light 401 may approach the flow cover 410 from different angles.

Also shown, the flow cover 410 may include inlet and outlet ports 420, 422 that are configured to fluidically engage other ports (not shown). For example, the other ports may be from the cartridge 302 (FIG. 4) or the workstation 300 (FIG. 4). The flow channel 418 is sized and shaped to direct a fluid along the detector surface 412. The height $H_1$ and other dimensions of the flow channel 418 may be configured to maintain a substantially even flow of a fluid along the detector surface 412. The dimensions of the flow channel 418 may also be configured to control bubble formation.

The sidewalls 406 and the flow cover 410 may be separate components that are coupled to each other. In other embodiments, the sidewalls 406 and the flow cover 410 may be integrally formed such that the sidewalls 406 and the flow cover 410 are formed from a continuous piece of material. By way of example, the flow cover 410 (or the flow cell 402) may comprise a transparent material, such as glass or plastic. The flow cover 410 may constitute a substantially rectangular block having a planar exterior surface and a planar inner surface that defines the flow channel 418. The block may be mounted onto the sidewalls 406. Alternatively, the flow cell 402 may be etched to define the flow cover 410 and the sidewalls 406. For example, a recess may be etched into the transparent material. When the etched material is mounted to the detection device 404, the recess may become the flow channel 418.

The detection device 404 has a detector surface 412 that may be functionalized (e.g., chemically or physically modified in a suitable manner for conducting designated reactions). For example, the detector surface 412 may be functionalized and may include a plurality of reaction sites 414 having one or more biomolecules immobilized thereto. The detector surface 412 has an array of reaction recesses or open-sided reaction chambers 408. Each of the reaction recesses 408 may include one or more of the reaction sites 414. The reaction recesses 408 may be defined by, for example, an indent or change in depth along the detector surface 412. In other embodiments, the detector surface 412 may be substantially planar.

As shown in FIG. 7, the reaction sites 414 may be distributed in a pattern along the detector surface 412. For instance, the reactions sites 414 may be located in rows and columns along the detector surface 412 in a manner that is similar to a microarray. However, it is understood that various patterns of reaction sites may be used. The reaction sites may include biological or chemical substances that emit light signals. For example, the biological or chemical substances of the reactions sites may generate light emissions in response to the excitation light 401. In particular embodiments, the reaction sites 414 include clusters or colonies of biomolecules (e.g., oligonucleotides) that are immobilized on the detector surface 412.

Figure 8:
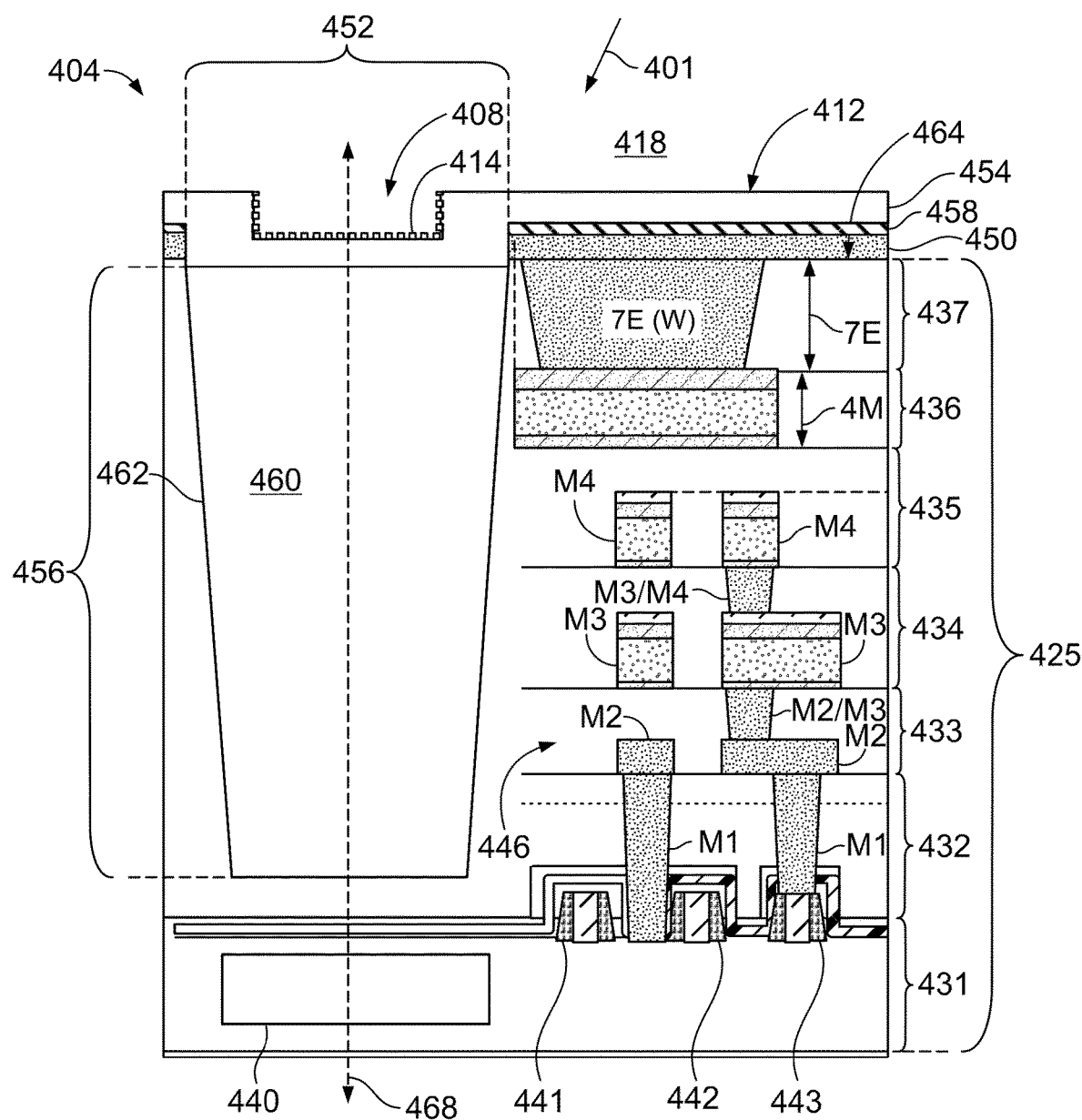
FIG. 8 is an enlarged portion of the cross-section of FIG. 7 illustrating the biosensor in greater detail.

FIG. 8 is an enlarged cross-section of the detection device 404 showing various features in greater detail. More specifically, FIG. 8 shows a single light sensor 440, a single light guide 462 for directing light emissions toward the light sensor 440, and associated circuitry 446 for transmitting signals based on the light emissions (e.g., photons) detected by the light sensor 440. It is understood that the other light sensors 440 of the sensor array 424 (FIG. 7) and associated components may be configured in an identical or similar manner. It is also understood, however, the detection device 404 is not required to be manufactured identically or uniformly throughout. Instead, one or more light sensors 440 and/or associated components may be manufactured differently or have different relationships with respect to one another.

The circuitry 446 may include interconnected conductive elements (e.g., conductors, traces, vias, interconnects, etc.) that are capable of conducting electrical current, such as the transmission of data signals that are based on detected photons. For example, in some embodiments, the circuitry 446 may be similar to or include a microcircuit arrangement, such as the microcircuit arrangement described in U.S. Pat. No. 7,595,883, which is incorporated herein by reference in the entirety. The detection device 404 and/or the device base 425 may comprise an integrated circuit having a planar array of the light sensors 440. The circuitry 446 formed within the detection device 425 may be configured for at least one of signal amplification, digitization, storage, and processing. The circuitry may collect and analyze the detected light emissions and generate data signals for communicating detection data to a bioassay system. The circuitry 446 may also perform additional analog and/or digital signal processing in the detection device 404.

The device base 425 may be manufactured using integrated circuit manufacturing processes, such as processes used to manufacture complementary-metal-oxide semiconductors (CMOSs). For example, the device base 425 may include a plurality of stacked layers 431-437 including a sensor layer or base 431, which is a silicon layer or wafer in the illustrated embodiment. The sensor layer 431 may include the light sensor 440 and gates 441-443 that are formed with the sensor layer 431. The gates 441-443 are electrically coupled to the light sensor 440. When the detection device 404 is fully formed as shown in FIGS. 7 and 8, the light sensor 440 may be electrically coupled to the circuitry 446 through the gates 441-443.

As used herein, the term "layer" is not limited to a single continuous body of material unless otherwise noted. For example, the sensor layer 431 may include multiple sub-layers that are different materials and/or may include coatings, adhesives, and the like. Furthermore, one or more of the layers (or sub-layers) may be modified (e.g., etched, deposited with material, etc.) to provide the features described herein.

In some embodiments, each light sensor 440 has a detection area that is less than about 50 $\mu m^2$. In particular embodiments, the detection area is less than about 10 $\mu m^2$. In more particular embodiments, the detection area is about 2 $\mu m^2$. In such cases, the light sensor 440 may constitute a single pixel. An average read noise of each pixel in a light sensor 440 may be, for example, less than about 150 electrons. In more particular embodiments, the read noise may be less than about 5 electrons. The resolution of the array of light sensors 440 may be greater than about 0.5 megapixels (Mpixels). In more specific embodiments, the resolution may be greater than about 5 Mpixels and, more particularly, greater than about 10 Mpixels.

The device layers also include a plurality of metal-dielectric layers 432-437, which are hereinafter referred to as substrate layers. In the illustrated embodiment, each of the substrate layers 432-437 includes metallic elements (e.g., W (tungsten), Cu (copper), or Al (aluminum)) and dielectric material (e.g., $SiO_2$). Various metallic elements and dielectric material may be used, such as those suitable for integrated circuit manufacturing. However, in other embodiments, one or more of the substrate layers 432-437 may include only dielectric material, such as one or more layers of $SiO_2$.

With respect to the specific embodiment shown in FIG. 8, the first substrate layer 432 may include metallic elements referred to as M1 that are embedded within dielectric material (e.g., $SiO_2$). The metallic elements M1 comprise, for example, W (tungsten). The metallic elements M1 extend entirely through the substrate layer 432 in the illustrated embodiment. The second substrate layer 433 includes metallic elements M2 and dielectric material as well as a metallic interconnects (M2/M3). The third substrate layer 434 includes metallic elements M3 and metal interconnects (M3/M4). The fourth substrate layer 435 also includes metallic elements M4. The device base 425 also includes fifth and sixth substrate layers 436, 437, which are described in greater detail below.

As shown, the metallic elements and interconnects are connected to each other to form at least a portion of the circuitry 446. In the illustrated embodiment, the metallic elements M1, M2, M3, M4 include W (tungsten), Cu (copper), and/or aluminum (Al) and the metal interconnects M2/M3 and M3/M4 include W (tungsten), but it is understood that other materials and configurations may be used. It is also noted that the device base 425 and the detection device 404 shown in FIGS. 7 and 8 are for illustrative purposes only. For example, other embodiments may include fewer or additional layers than those shown in FIGS. 7 and 8 and/or different configurations of metallic elements.

In some embodiments, the detection device 404 includes a shield layer 450 that extends along an outer surface 464 of the device base 425. In the illustrated embodiment, the shield layer 450 is deposited directly along the outer surface 464 of the substrate layer 437. However, an intervening layer may be disposed between the substrate layer 437 and the shield layer 450 in other embodiments. The shield layer 450 may include a material that is configured to block, reflect, and/or significantly attenuate the light signals that are propagating from the flow channel 418. The light signals may be the excitation light 401 and/or the light emissions 466 (shown in FIG. 9). By way of example only, the shield layer 450 may comprise tungsten (W).

As shown in FIG. 8, the shield layer 450 includes an aperture or opening 452 therethrough. The shield layer 450 may include an array of such apertures 452. In some embodiments, the shield layer 450 may extend continuously between adjacent apertures 452. As such, the light signals from the flow channel 418 may be blocked, reflected, and/or significantly attenuated to prevent detection of such light signals by the light sensors 440. However, in other embodiments, the shield layer 450 does not extend continuously between the adjacent apertures 452 such then one or more openings other than the apertures 452 exits in the shield layer 450.

The detection device 404 may also include a passivation layer 454 that extends along the shield layer 450 and across the apertures 452. The shield layer 450 may extend over the apertures 452 thereby directly or indirectly covering the apertures 452. The shield layer 450 may be located between the passivation layer 454 and the device base 425. An adhesive or promoter layer 458 may be located therebetween to facilitate coupling the passivation and shield layers 454, 450. The passivation layer 454 may be configured to protect the device base 425 and the shield layer 450 from the fluidic environment of the flow channel 418.

In some cases, the passivation layer 454 may also be configured to provide a solid surface (i.e., the detector surface 412) that permits biomolecules or other analytes-of-interest to be immobilized thereon. For example, each of the reaction sites 414 may include a cluster of biomolecules that are immobilized to the detector surface 412 of the passivation layer 454. Thus, the passivation layer 454 may be formed from a material that permits the reaction sites 414 to be immobilized thereto. The passivation layer 454 may also comprise a material that is at least transparent to a desired fluorescent light. By way of example, the passivation layer 454 may include silicon nitride ($Si_3N_4$) and/or silica ($SiO_2$). However, other suitable material(s) may be used. In addition, the passivation layer 454 may be physically or chemically modified to facilitate immobilizing the biomolecules and/or to facilitate detection of the light emissions.

In the illustrated embodiment, a portion of the passivation layer 454 extends along the shield layer 450 and a portion of the passivation layer 454 extends directly along filter material 460 of a light guide 462. The reaction recess 408 may be formed directly over the light guide 462. In some cases, prior to the passivation layer 454 being deposited along the shield layer 450 or adhesion layer 458, a base hole or cavity 456 may be formed within the device base 425. For example, the device base 425 may be etched to form an array of the base holes 456. In particular embodiments, the base hole 456 is an elongated space that extends from proximate the aperture 452 toward the light sensor 440. The base hole may extend lengthwise along a central longitudinal axis 468. A three-dimensional shape of the base hole 456 may be substantially cylindrical or frustro-conical in some embodiments such that a cross-section taken along a plane that extends into the page of FIG. 8 is substantially circular. The longitudinal axis 468 may extend through a geometric center of the cross-section. However, other geometries may be used in alternative embodiments. For example, the cross-section may be substantially square-shaped or octagonal.

The filter material 460 may be deposited within the base hole 456 after the base hole 456 is formed. The filter material 460 may form (e.g., after curing) a light guide 462. The light guide 462 is configured to filter the excitation light 401 and permit the light emissions 466 to propagate therethrough toward the corresponding light sensor 440. The light guide 462 may be, for example, an organic absorption filter. By way of specific example only, the excitation light may be about 532 nm and the light emissions may be about 570 nm or more.

In some cases, the organic filter material may be incompatible with other materials of the biosensor. For example, organic filter material may have a coefficient of thermal expansion that causes the filter material to significantly expand. Alternatively or in addition to, the filter material may be unable to sufficiently adhere to certain layers, such as the shield layer (or other metal layers). Expansion of the filter material may cause mechanical stress on the layers that are adjacent to the filter material or structurally connected to the filter material. In some cases, the expansion may cause cracks or other unwanted features in the structure of the biosensor. As such, embodiments set forth herein may limit the degree to which the filter material expands and/or the degree to which the filter material is in contact with other layers. For example, the filter material of different light guides may be isolated from each other by the passivation layer. In such embodiments, the filter material may not contact the metal layer(s). Moreover, the passivation layer may resist expansion and/or permit some expansion while reducing generation of unwanted structural features (e.g., cracks).

The light guide 462 may be configured relative to surrounding material of the device base 425 (e.g., the dielectric material) to form a light-guiding structure. For example, the light guide 462 may have a refractive index of about 2.0 so that the light emissions are substantially reflected at an interface between the light guide 462 and the material of the device base 425. In certain embodiments, the light guide 462 is configured such that the optical density (OD) or absorbance of the excitation light is at least about 4 OD. More specifically, the filter material may be selected and the light guide 462 may be dimensioned to achieve at least 4 OD. In more particular embodiments, the light guide 462 may be configured to achieve at least about 5 OD or at least about 6 OD. Other features of the biosensor 400 may be configured to reduce electrical and optical crosstalk.

Figure 9:
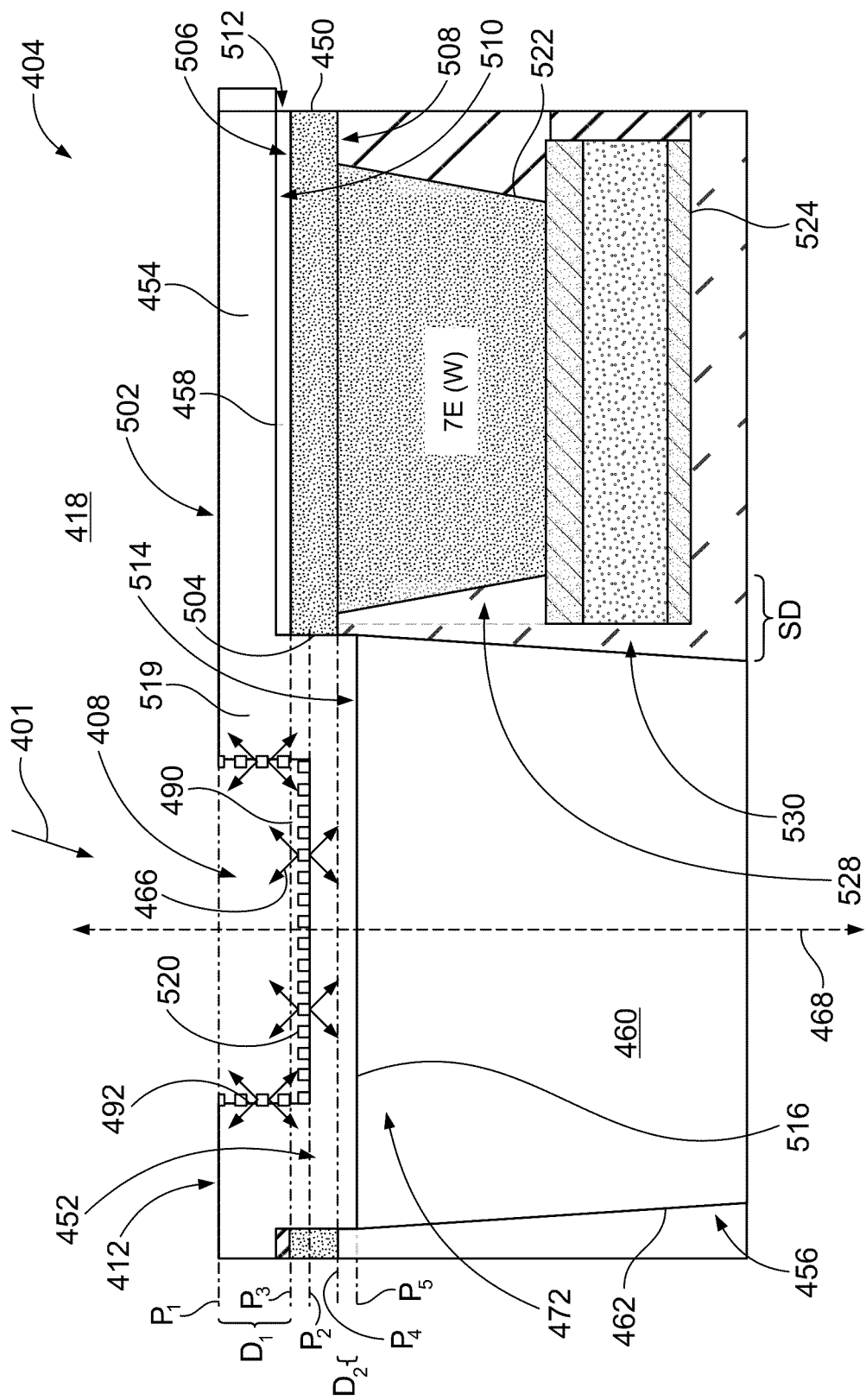
FIG. 9 is another enlarged portion of the cross-section of FIG. 7 illustrating the biosensor in greater detail.

FIG. 9 illustrates an enlarged view of the detector surface 412 and portions of the detection device 404 (FIG. 7) that are located proximate to the detector surface 412. More specifically, the passivation layer 454, the adhesion layer 458, the shield layer 450, and the light guide 462 are shown in FIG.

9. Each of the layers may have a outer (top) surface or an inner (bottom) surface and may extend along an adjacent layer at an interface. In some embodiments, the detector surface 412 is configured to form the reaction recess 408 proximate to the aperture 452. The reaction recess 408 may be, for example, an indent, pit, well, groove, or open-sided chamber or channel. Alternatively, the detector surface 412 may be planar without the recesses shown in FIGS. 7-9. As shown, the aperture 452 is defined by an aperture or layer edge 504. The layer edge 504 faces radially inward toward the longitudinal axis 468.

The detector surface 412 may include an elevated portion 502 and the reaction recess 408 may include a base surface 490. The base surface 490 may extend substantially parallel to the shield layer 450. The detector surface 412 may also include a side surface 492 that extends substantially orthogonal to the base surface 490 and the elevated portion 502 of the detector surface 412. The side surface 492 may define a periphery of the reaction recess 408. Although the elevated portion 502, the base surface 490, and the side surface 492 are referenced as separate surfaces it is understood that the surfaces may be portions of the detector surface 412. Moreover, it is understood that, due to manufacturing tolerances, the surfaces may not have be readily distinct. For example, in other embodiments, the base surface 490 and the side surface 492 may be substantially a single surface with a concave shape.

The base surface 490 may represent (or include a point that represents) a deepest portion of the passivation layer 454 along the detector surface 412 within the reaction recess 408. For example, the elevated portion 502 may extend along a surface plane $P_1$ and the base surface 490 may extend along a surface plane $P_2$. As shown, the surface planes $P_1$ and $P_2$ are offset with respect to each other by a depth or distance $D_1$. The surface plane $P_2$ is closer to the light guide 462 or the light sensor 440 (FIG. 7) than the surface plane $P_1$. In the illustrated embodiment, the depth $D_1$ of the base surface 490 is substantially continuous due to the base surface 490 being substantially planar. In other embodiment, however, the depth $D_1$ may vary. For example, the base surface 490 may have a concave shape with the depth increasing as the base surface 490 extends toward a center or middle thereof.

The reaction recess 408 may extend toward or be located within the aperture 452. For instance, at least a portion of the base surface 490 may reside within the aperture 452. The shield layer 450 may have an outer surface 506 that faces the passivation layer 454 and an inner surface 508 that faces the device base 425. The outer surface 506 may extend along a surface plane $P_3$, and the inner surface 508 may extend along a surface plane $P_4$. The distance between the surface planes $P_3$ and $P_4$ may represent a thickness of the shield layer 450. As shown, the surface plane $P_3$ may be located between the surface planes $P_1$, $P_2$. As such, the base surface 490 extends within the aperture 452 as defined by the layer edge 504. In other embodiments, however, the surface plane $P_2$ may be located above the surface plane $P_3$ such that the base surface 490 does not reside within the aperture 452. Moreover, in some embodiments, the surface plane $P_2$ may be located below the surface plane $P_4$ such that base surface 490 is located below the aperture 452.

The passivation layer 454 includes the detector surface 412 and an inner surface 510 that extends along the outer surface 506 of the shield layer 450 at an interface 512. In some embodiments, the adhesion layer 458 may extend along and define the interface 512 between the shield layer 450 and the passivation layer 454.

In the illustrated embodiment, the passivation layer 454 extends directly along the light guide 462. More specifically, the inner surface 510 of the passivation layer 454 may directly engage a material surface 514 of the light guide 462. As used herein, the phrase "directly engage" and the like may include the two layers directly contacting each other or the two layers being bonded to each other through the use of an adhesion promoter material(s). The light guide 462 has an input region 472 that includes the material surface 514. The input region 472 may represent a portion of the light guide 462 that initially receives the light emissions.

The inner surface 510 may directly engage the material surface 514 at an interface 516. The interface 516 may represent a material level of the filter material 460 that is deposited within the guide cavity 456 (FIG. 7). In the illustrated embodiment, the interface 516 is substantially planar such that the interface 516 extends along an interface plane $P_5$. The interface plane $P_5$ may extend substantially parallel to one or more of the surface planes $P_1$, $P_2$, $P_3$, $P_4$. In other embodiments, however, the interface 516 may have a concave shape such that the interface 516 bows toward the light sensor 440 (FIG. 8) or in an opposite direction away from the light sensor 440.

The passivation layer 454 may fill a void generated when the aperture 452 is formed. Thus, in some embodiments, the passivation layer 454 may be located within or reside in the aperture 452. In particular embodiments, the interface 516 may be located a depth $D_2$ into the device base 425. In particular embodiments, the depth $D_2$ may be configured such that the interface 516 is located below the aperture 452 as shown in FIG. 8. In such embodiments, the passivation layer 454 may isolate (e.g., separate) the filter material 460 and the shield layer 450. Such embodiments may be suitable when the filter material 460 and the shield layer 450 are incompatible such that cracks or other unwanted features may develop during manufacture of usage of the biosensor 400 (FIG. 7). In other embodiments, at least a portion of the interface 516 may be located within the aperture 452.

Also shown in FIG. 9, the passivation layer 454 may form a joint or corner region 519. The joint region 519 may include the side surface 492 and extend around the longitudinal axis 468. The joint region 519 may include a relatively thicker portion of the passivation layer 454 that extends from the elevated portion 502 to the inner surface 510 at the material interface 516 (or between the surface plane $P_1$ and the interface plane $P_5$). The dimensions of the joint region 519 may resist mechanical stresses caused by expansion of the filter material 460 during manufacture of the biosensor 400 and/or during thermal cycling that may occur during designated protocols (e.g., SBS sequencing). As shown, the thickness between the surface plane $P_1$ and the interface plane $P_5$ is more than twice the thickness between the elevated portion 502 of the detector surface 412 and the interface 512.

The reaction site 414 may include biological or chemical substances, which are generally represented as dots 520 in FIG. 9. The biological or chemical substances may be immobilized to the detector surface 412 or, more specifically, the base and side surfaces 490, 492. In particular embodiments, the reaction site 414 is located proximate to the aperture 452 so that light emissions propagate through the passivation layer 454, through the aperture 452, and into the input region 472 of the light guide 462.

In some embodiments, the reaction sites 414 or the biological or chemical substances 520 therein may be patterned such that the reaction sites 414 or substances 520 have predetermined locations. For example, after the passivation layer 454 is applied, the reaction sites 414 or portions thereof may be patterned onto the passivation layer 454. In the illustrate embodiment, each aperture 452 is associated with a single reaction site 414 such that the light emissions from the reaction site 414 are directed toward the corresponding light sensor 440. The biological or chemical substances 520 in a single reaction site 414 may be similar or identical (e.g., a colony of oligonucleotides that have a common sequence). However, in other embodiments, more than one reaction site 414 may correspond to one of the apertures 452.

In particular embodiments, the reaction sites 414 may include pads or metal regions that are described in U.S. Provisional Application No. 61/495,266, filed on Jun. 9, 2011, and U.S. Provisional Application No. 61/552,712, filed on Oct. 28, 2011. Each of the U.S. Provisional Application No. 61/495,266 (the '266 Application) and the U.S. Provisional Application No. 61/552,712 (the '712 Application) is incorporated herein by reference in its entirety. In some embodiments, the reaction sites 414 may be fabricated after the flow cell 402 (FIG. 7) is manufactured on the detection device 404.

In the illustrated embodiment, the reaction site 414 includes a colony of oligonucleotides 520 in which the oligonucleotides have an effectively common sequence. In such embodiments, each of the oligonucleotides may generate common light emissions when the excitation light 401 is absorbed by the fluorophores incorporated within the oligonucleotides. As shown, the light emissions 466 may emit in all directions (e.g., isotropically) such that, for example, a portion of the light is directed into the light guide 462, a portion of the light is directed to reflect off the shield layer 450, and a portion of the light is directed into the flow channel 418 or the passivation layer 454. For the portion that is directed into the light guide 462, embodiments described herein may be configured to facilitate detection of the photons.

Also shown in FIG. 9, the device base 425 may include peripheral crosstalk shields 522, 524 located within the device base 425. The crosstalk shields 522, 524 may be positioned relative to the light guide 462 and configured so that the crosstalk shields 522, 524 block or reflect light signals propagating out of the light guide 462. The light signals may include the excitation light 401 that has been reflected or refracted and/or the light emissions 466 generated at or proximate to the detector surface 412. In some embodiments, the crosstalk shields 522, 524 may also directly block the excitation light 401 from the flow channel 418. As such, the crosstalk shields 522, 524 may reduce detection of unwanted light signals. For example, the crosstalk shields 522, 524 may reduce optical crosstalk between adjacent light sensors 440 and/or may improve collection efficiency of the corresponding light sensor 440. The crosstalk shields 522, 524 may be, for example, metallic elements that are fabricated during the manufacture of the device base 425. In some embodiments, the processes used to fabricate the M1, M2, M3, M2/M3, and M3/M4 elements of the circuitry 446 (FIG. 8) may be the same as or similar to the processes that fabricate the crosstalk shields 522, 524. For example, the crosstalk shields 522, 524 may be located within dielectric material (e.g., dielectric layers) of the device base 425 and comprise the same material that is used to fabricate the circuitry 446 (e.g., one or more of the materials used to fabricate the M1, M2, M3, M2/M3, and M3/M4 elements). Although not shown, in some cases, the different stages of CMOS manufacture may include forming the metallic elements that will transmit data signals while also forming the crosstalk shields.

Although the crosstalk shields 522, 524 may be manufactured in a similar manner as the circuitry 446, the crosstalk shields 522, 524 may be electrically separate from the circuitry 446. In other words, for some embodiments, the crosstalk shields 522, 524 may not transmit data signals. In other embodiments, however, the crosstalk shields 522, 524 may be traces or other metallic elements that are configured to transmit data signals. As also shown in FIG. 9, the crosstalk shields 522, 524 may have different cross-sectional dimensions (e.g., width, height or thickness) and shapes and may also be fabricated from different materials.

In the illustrated embodiment, the crosstalk shields 522, 524 are coupled to each other to form a single larger crosstalk shield. However, the crosstalk shields 522, 524 may be spaced apart from each other in other configurations. For example, the crosstalk shields 522, 524 may be spaced apart from each other along the longitudinal axis 468. In the illustrated embodiment, the crosstalk shields 522, 524 at least partially surround the input region 472 and a portion of the passivation layer 454. The crosstalk shield 522 directly engages the shield layer 450. In some embodiments, the crosstalk shields 522, 524 may only partially surround the light guide 462. In other embodiments, the crosstalk shields 522, 524 may constitute crosstalk rings that circumferentially surround the entire light guide 462. Such embodiments are described in greater detail below with respect to FIGS. 10 and 11.

As shown, the guide cavity 456 is defined by one or more interior surfaces 526 of the device base 425. In particular embodiments, the interior surfaces 526 may be surface(s) of the dielectric material (e.g., $SiO_2$) from the substrate layers 432-437. The crosstalk shields 522, 524 may directly abut the light guide such that a portion of the metallic elements is exposed to and directly engages the filter material 460 of the light guide 462. In other embodiments, however, the crosstalk shields 522, 524 are not exposed to the light guide 462 and, instead, may be positioned immediately adjacent to the light guide 462 such that a portion of the dielectric material is located between the crosstalk shields 522, 524 and the light guide 462. For example, in the illustrated embodiment, dielectric material 528, 530 is located between the light guide 462 and the crosstalk shields 522, 524, respectively. The dielectric material 528, 530 may each include a portion of the interior surface 526. The dielectric material 528, 530 may separate the light guide 462 from the respective crosstalk shields 522, 524 by a separation distance SD. By way of example only, the separation distance SD may be at least about 150 nm. In some embodiments, the separation distance SD is at least about 100 nm. The separation distance SD may be less than 100 nm.

Figure 10:
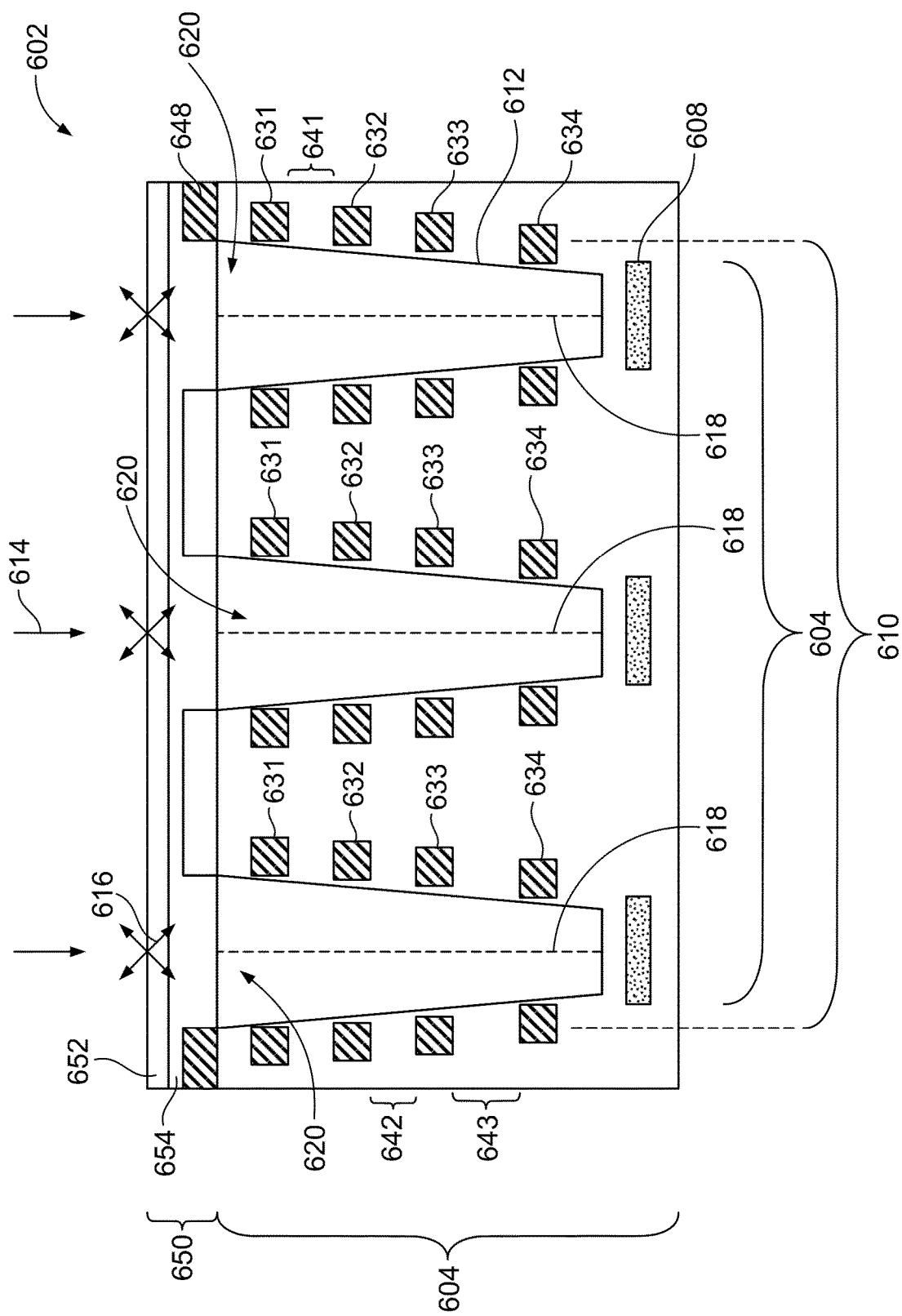
FIG. 10 is a schematic cross-section of a detection device formed in accordance with another embodiment.

FIG. 10 is a schematic cross-section of a detection device 602 formed in accordance with another embodiment. The detection device 602 may include similar features as the detection device 404 (FIG. 7) and may be used in biosensors, such as the biosensor 400 (FIG. 7) or the biosensor 102 (FIG. 1). The detection device 602 may also be manufactured using integrated circuit manufacturing technologies. The detection device 602 is described and illustrated to demonstrate other features that detection devices and biosensors may have. In some embodiments, the detection device 602 alone may constitute a biosensor. In other embodiments, the detection device 602 may be coupled to a flow cell to form a biosensor. For example, the detection device 602 may be coupled to the flow cell 402 and form a flow channel between the detection device 602 and the flow cell 402.

As shown, the detection device 602 includes a device base 604, a shield layer 640, and multiple sub-layers 652, 654 that collectively form a passivation layer 650 of the detection device 602. The device base 604 includes a sensor array 606 of light sensors 608 and a guide array 610 of light guides 612. The light sensors 608 may be similar or identical to the light sensors 440, and the light guides 612 may be similar or identical to the light guides 462. For example, the light guides 612 are configured to receive the excitation light 614 and the light emissions 616. As shown, the light emissions 616 are illustrated as light being emitted from a single point. It is understood that the light emissions may be generated from multiple points along the passivation layer 650. Each of the light guides 612 extends into the device base 604 along a central longitudinal axis 618 from an input region 620 of the light guide 612 toward a corresponding light sensor 608 of the sensor array 606.

Similar to the light guides 462, the light guides 612 may include a filter material that is configured to filter the excitation light 614 and permit the light emissions 616 to propagate therethrough toward the corresponding light sensors 608. The device base 604 includes device circuitry (not shown) that is electrically coupled to the light sensors 608 and configured to transmit data signals based on photons detected by the light sensors. Although not shown in FIGS. 10 and 11, the circuitry of the device base 604 may be located between the light guides 612 similar to the circuitry 446 (FIG. 8) located between the light guides 462.

As shown, the device base 604 includes peripheral crosstalk shields 631-634 that are located within the device base 604. More specifically, each of the light guides 612 is surrounded by multiple crosstalk shields 631-634. The crosstalk shields 631-634 for each of the light guides 612 may be spaced apart from each other along the respective longitudinal axis 618 such that gaps 641-643 are formed therebetween. The sizes of the gaps 641-643 may be substantially equal to one another or may differ. For example, the gaps 643 are slightly larger than the gaps 642.

In the illustrated embodiment, the crosstalk shields 631-634 are configured to circumferentially surround the light guides 612. As used herein, the phrase "circumferentially surround" is not intended to require that the light guides 612 have circular cross-section and/or the crosstalk shields 631-634 have circular shapes. Instead, a crosstalk shield may circumferentially surround the light guide 612 if the crosstalk shield surrounds the corresponding longitudinal axis 618. The crosstalk shield may completely surround the longitudinal axis 618 or only partially surround the longitudinal axis 618. For example, the crosstalk shields 631-634 may continuously extend around the corresponding light guide 612 or, in other cases, the crosstalk shields 631-634 may include multiple sub-elements that are individually distributed around the light guide 612 to at least partially surround the corresponding light guide.

Similar to the shield layer 452, the shield layer 640 may form apertures 642 therethrough. The apertures 642 are substantially aligned with corresponding light guides 612 and light sensors 608 to permit light signals to propagate into the corresponding input regions 620. The sub-layer 654 may be deposited over the shield layer 640 such that the material of the sub-layer 654 fills at least a portion of the apertures. In some embodiments, an additional sub-layer 652 is deposited over the sub-layer 654 to form the passivation layer 650. By way of example only, either of the sub-layers 652, 654 may include plasma vapor deposition (PVD) Ta$_2$O$_5$ or plasma-enhanced chemical vapor deposition (PECVD) Si$_x$N$_y$. In another embodiment, an additional sub-layer may be stacked onto the sub-layers 652, 654. By way of one specific example, the sub-layer 654 may be PVD Ta$_2$O$_5$, the sub-layer 652 may be PECVD Si$_x$N$_y$, and an additional layer that is stacked onto the sub-layer 652 may be PVD Ta$_2$O$_5$.

Figure 11:
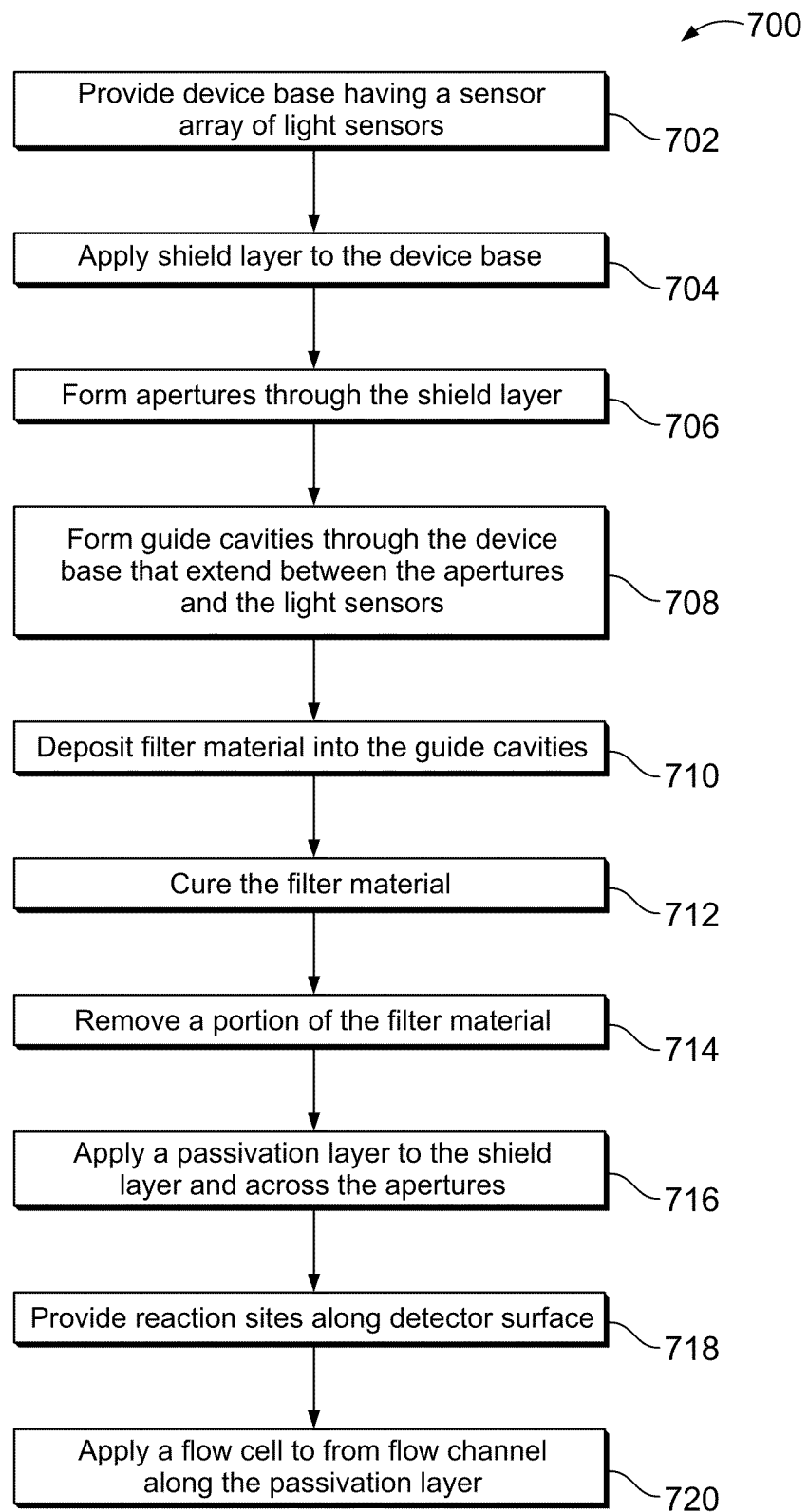
FIG. 11 is a flowchart illustrating a method of manufacturing a biosensor in accordance with an embodiment.
Figure 12A:
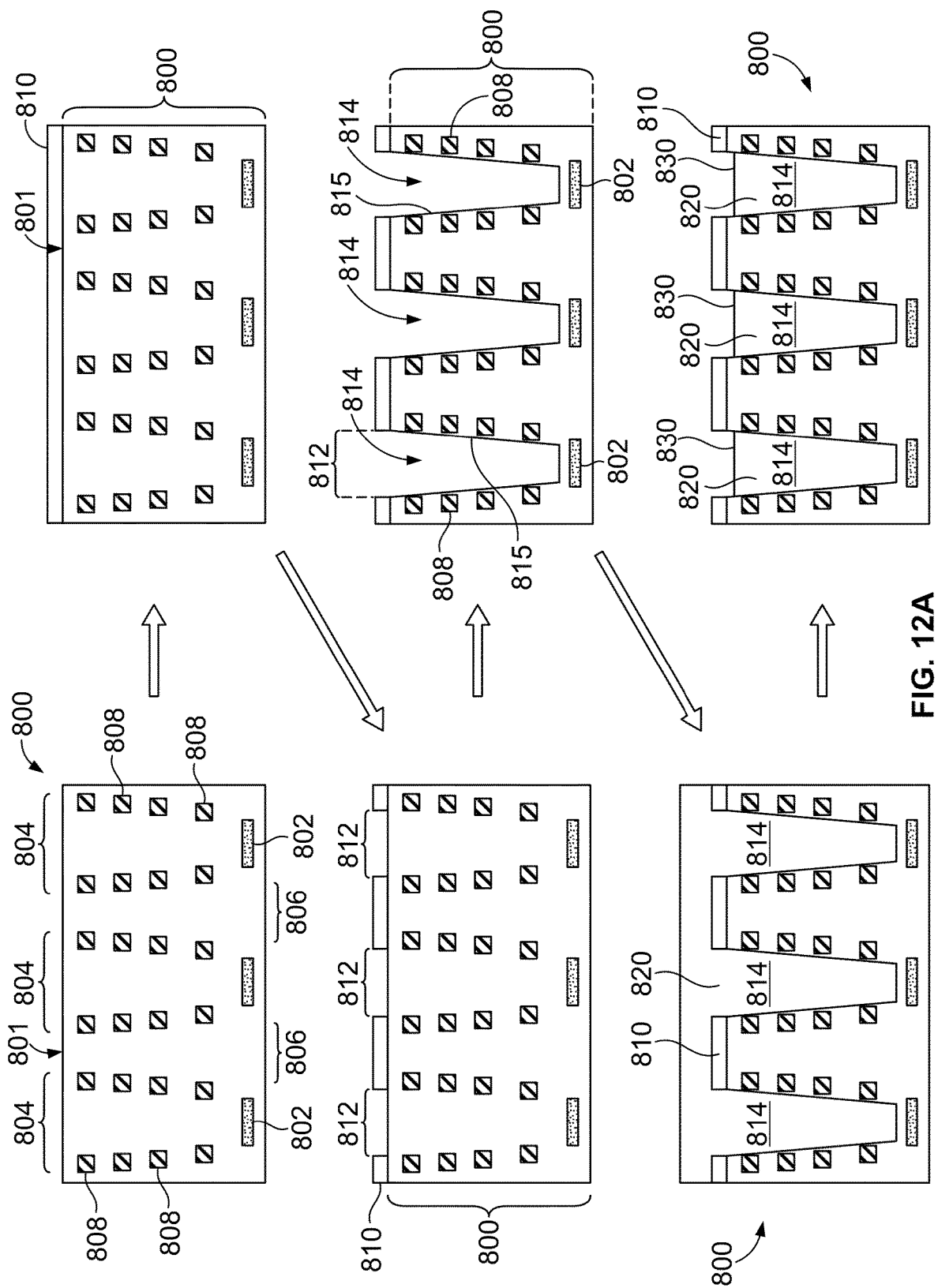
FIGS. 12A and 12B illustrate different stages of manufacturing the biosensor of FIG. 11.
Figure 12B:
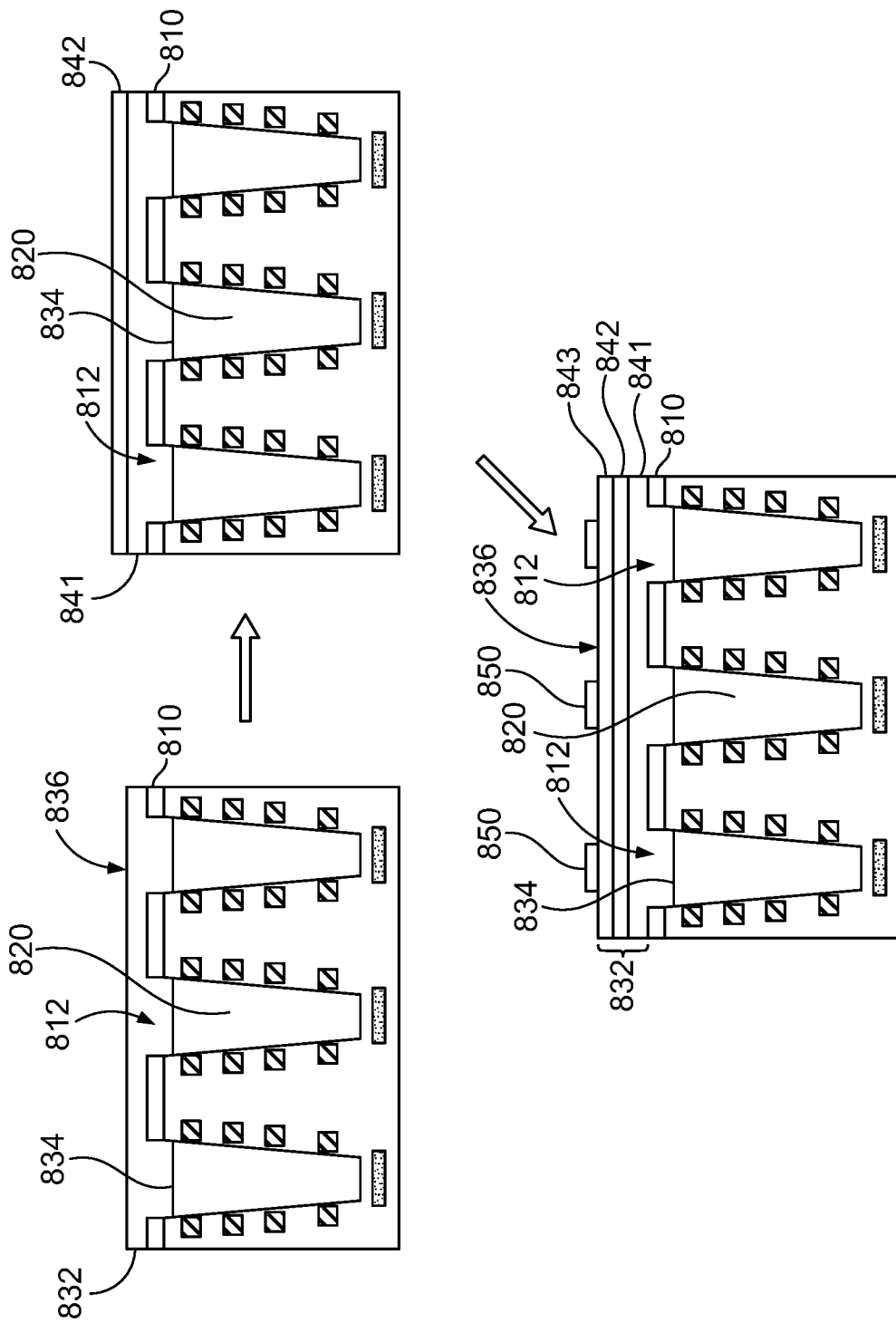

FIG. 11 is a flowchart illustrating a method 700 of manufacturing a biosensor in accordance with one embodiment. The method 700 is illustrated in FIGS. 12A and 12B. The method 700, for example, may employ structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion.

The method 700 may include providing (at 702) a device base 800 having a sensor array of light sensors 802. As shown, the device base 800 has an outer or external surface 801. The device base 800 may be manufactured using integrated circuit manufacturing technologies, such as CMOS manufacturing technologies. For example, the device base 800 may include several substrate layers with different modified features (e.g., metallic elements) embedded therein. In some embodiments, the device base 800 may include guide regions 804 and circuitry regions 806. The guide regions 804 may correspond to portions of the device base 800 that will include, after the method 700, the light guides. Adjacent guide regions 804 may be separated by the circuitry regions 806 that include device circuitry (not shown), which may be similar to the device circuitry described herein. More specifically, the device circuitry may be electrically coupled to the light sensors 802 and configured to transmit data signals based on photons detected by the light sensors 802. In some embodiments, the guide regions 804 may include peripheral crosstalk shields 808 that surround substrate material in the guide regions 804.

The method 700 may also include applying (at 704) a shield layer 810 to the outer surface 801 of the device base 800 and forming (at 706) apertures 812 through the shield layer 810. As described above, the shield layer 810 may include a metal material that is configured to block light signals. The apertures 812 may be formed by applying a mask (not shown) and removing material (e.g., through etching) of the shield layer 810 to form the apertures 812.

At 708, guide cavities 814 may be formed in the device base 800. More specifically, the substrate material within the guide regions 804 may be removed so that the guide cavities 814 extend from proximate to the apertures 812 toward corresponding light sensors 802. As shown in FIG. 12A, interior surfaces 815 of the substrate material may define the guide cavities 814. The guide cavities 814 may be sized and shaped such that the interior surfaces 815 are proximate to the crosstalk shields 808. As described herein, the crosstalk shields 808 may be immediately adjacent to the interior surfaces 815 or may be exposed in the guide cavities 814.

The method 700 may also include depositing (at 710) filter material 820 within the guide cavities 814. The filter material 820 may be, for example, an organic filter material. In some embodiments, a portion of the filter material 820 may extend along the shield layer 810 after the depositing operation. For example, the amount of the filter material 820 applied to the device base 800 may exceed the available volume within the guide cavities 814. As such, the filter material 820 may overflow the guide cavities 814 and extend along the shield layer 810.

In some embodiments, depositing (at 710) the filter material 820 may include pressing (e.g., using a squeegee-like component) the filter material 820 into the guide cavities 814. FIG. 12A appears to indicate a uniform layer of the filter material 820 along the shield layer 810. In some embodiments, the layer of filter material 820 may not be uniform. For instance, only portions of the shield layer 810 may have the filter material 820 thereon. In alternative embodiments, the depositing operation may include selectively filling each of the guide cavities 814 such that the filter material 820 does not clear or overflow the guide cavities 814.

At 712, the filter material 820 may be cured. Optionally, the method 700 may also include removing (at 714) the filter material 820 from the shield layer 810 and, in some cases, portions of the filter material 820 from the guide cavities 814. The filter material 820 may be removed from within the guide cavities 814 so that a material level 830 of the filter material 820 is located within the aperture 812 or at a depth below the shield layer 810. In embodiments where the material level 830 is below the shield layer 810, the filter material 820 may not contact any material of the shield layer 810. The filter material 820 within the guide cavities 814 may form light guides. Different processes may be implemented for removing the filter material 820 from the shield layer 810. For example, the removing operation may include at least one of etching the filter material or chemically polishing the filter material.

As shown in FIG. 12B, the method 700 may also include applying (at 716) a passivation layer 832 to the shield layer 810 and to the filter material 820 of the light guides such that the passivation layer 832 extends directly along the shield layer 810 and across the apertures 812. The passivation layer 832 may extend directly along the light guides at corresponding material interfaces 834, such as the material interfaces 516 (FIG. 9). In the illustrated embodiment, the passivation layer 832 has a planar detector surface 836. In other embodiments, the detector surface 836 may form an array of reaction recesses, such as the reaction recesses 408 (FIG. 7). The reaction recesses may extend toward or be located within corresponding apertures 812.

In some embodiments, the passivation layer 832 includes multiple sub-layers 841-843. In particular embodiments, at least one of the sub-layers 841-843 includes tantalum. For example, the sub-layer 841 may include tantalum pentoxide ($Ta_2O_5$), the sub-layer 842 may include a low-temperature film (e.g., silicon nitride ($Si_xN_y$)), and the sub-layer 843, which may have the detector surface 836, may include tantalum pentoxide ($Ta_2O_5$). However, the sub-layers 841-843 are only provided as examples and other passivation layers may include fewer sub-layers, more sub-layers, or sub-layers with different materials. In some cases, only a single sub-layer is used for the passivation layer.

Optionally, the method 700 may include providing (at 718) reaction sites 850 and mounting a flow cell (not shown). Providing the reaction sites 850 may occur prior to or after the flow cell is coupled to the detection device. The reaction sites 850 may be located at designation addresses such that the reaction sites 850 have a predetermined pattern along the detector surface 836. The reaction sites may correspond (e.g., one site to one light sensor, one site to multiple light sensors, or multiple sites to one light sensor) in a predetermined manner. In other embodiments, the reaction sites may be randomly formed along the detector surface 836. As described herein, the reaction sites 850 may include biological or chemical substances immobilized to the detector surface 836. The biological or chemical substances may be configured to emit light signals in response to excitation light. In particular embodiments, the reaction sites 850 include clusters or colonies of biomolecules (e.g., oligonucleotides) that are immobilized on the detector surface 836.

In an embodiment, a biosensor is provided that includes a flow cell and a detection device having the flow cell coupled thereto. The flow cell and the detection device form a flow channel that is configured to have biological or chemical substances therein that generate light emissions in response to an excitation light. The detection device includes a device base having a sensor array of light sensors and a guide array of light guides. The light guides have input regions that are configured to receive the excitation light and the light emissions from the flow channel. The light guides extend into the device base from the input regions toward corresponding light sensors and have a filter material that is configured to filter the excitation light and permit the light emissions to propagate toward the corresponding light sensors. The device base includes device circuitry electrically coupled to the light sensors and configured to transmit data signals based on photons detected by the light sensors. The detection device also includes a shield layer that extends between the flow channel and the device base. The shield layer has apertures that are positioned relative to the input regions of corresponding light guides such that the light emissions propagate through the apertures into the corresponding input regions. The shield layer extends between adjacent apertures and is configured to block the excitation light and the light emissions incident on the shield layer between the adjacent apertures.

In one aspect, the input regions of the light guides may be located within the corresponding apertures of the shield layer or may be located a depth into the device base.

In another aspect, the detection device may include a passivation layer that extends along the shield layer such that the shield layer is between the passivation layer and the device base. The passivation layer may extend across the apertures.

In particular cases, the filter material of the light guides may be an organic filter material. The passivation layer may extend directly along the input regions of the light guides and isolate the organic filter material from the shield layer. The material interfaces may be located within the corresponding apertures of the shield layer or located a depth into the device base. In certain embodiments, the passivation layer extends into the apertures and forms an array of reaction recesses. The reaction recesses may extend toward or be located within corresponding apertures.

In certain embodiments, the biological or chemical substances are configured to be located within the reaction recesses. In certain embodiments, the reaction recesses have corresponding base surfaces. The base surfaces may be located within the aperture or located a depth into the device base.

In another aspect, the device base includes peripheral crosstalk shields. Each of the crosstalk shields may surround one of the corresponding light guides. The crosstalk shields may be configured to reduce optical crosstalk between adjacent light sensors.

In another aspect, the biosensor is lens-free such that the biosensor does not include an optical element that focuses the light emissions toward a focal point.

In an embodiment, a biosensor is provided that includes a flow cell and a detection device having the flow cell coupled thereto. The flow cell and the detection device form a flow channel that is configured to have biological or chemical substances therein that generate light emissions in response to an excitation light. The detection device may include a device base having a sensor array of light sensors and a guide array of light guides. The light guides are configured to receive the excitation light and the light emissions from the flow channel. Each of the light guides extends into the device base along a central longitudinal axis from an input region of the light guide toward a corresponding light sensor of the sensor array. The light guides include a filter material that is configured to filter the excitation light and permit the light emissions to propagate therethrough toward the corresponding light sensors. The device base includes device circuitry that is electrically coupled to the light sensors and configured to transmit data signals based on photons detected by the light sensors. The device base includes peripheral crosstalk shields located therein that surround corresponding light guides of the guide array. The crosstalk shields at least partially surround the corresponding light guides about the respective longitudinal axis to reduce optical crosstalk between adjacent light sensors.

In one aspect, the crosstalk shields may surround the input regions of the corresponding light guides.

In another aspect, the crosstalk shields may include crosstalk rings that circumferentially surround the corresponding light guide.

In another aspect, the device base may include a complementary-metal-oxide semiconductor (CMOS) and the device circuitry. The crosstalk shields may include metallic elements located within dielectric layers of the device base. The crosstalk shields may be electrically separate from the device circuitry.

In another aspect, a shield layer may extend between the flow channel and the device base. The shield layer may have apertures that are positioned relative to the input regions of corresponding light guides of the guide array. The apertures may permit the light emissions to propagate therethrough into the input regions. The shield layer may extend between adjacent apertures and is configured to block the excitation light and the light emissions incident on the shield layer between the adjacent apertures. For instance, the input regions of the light guides may be located within the corresponding apertures of the shield layer or are located a depth into the device base.

In another aspect, the detection device may also include a passivation layer that extends along the shield layer such that the shield layer is between the passivation layer and the device base and across the apertures.

In another aspect, the crosstalk shield abuts or is immediately adjacent to the shield layer.

In another aspect, the crosstalk shields are first crosstalk shields, and the device base includes second crosstalk shields in which each of the light guides of the guide array is at least partially surrounded by corresponding first and second crosstalk shields. For example, the first and second crosstalk shields may be spaced apart from each other along the corresponding longitudinal axis. In another embodiment, the first and second crosstalk shields have different dimensions.

In an embodiment, a method of manufacturing a biosensor is provided. The method includes providing a device base having a sensor array of light sensors and device circuitry that is electrically coupled to the light sensors and configured to transmit data signals based on photons detected by the light sensors. The device base has an outer surface. The method also includes applying a shield layer to the outer surface of the device base and forming apertures through the shield layer. The method also includes forming guide cavities that extend from corresponding apertures toward a corresponding light sensor of the sensor array and depositing filter material within the guide cavities. A portion of the filter material extends along the shield layer. The method also includes curing the filter material and removing the filter material from the shield layer. The filter material within the guide cavities forms light guides. The method also includes applying a passivation layer to the shield layer such that the passivation layer extends directly along the shield layer and across the apertures.

In one aspect, removing the filter material from the shield layer includes removing a portion of the filter material within the guide cavities such that a material level of the filter material is located within the aperture or at a depth below the shield layer.

In another aspect, the passivation layer extends directly along the light guides at corresponding material interfaces. The material interfaces are located within the corresponding apertures or located a depth into the device base.

In another aspect, the filter material is an organic filter material. The passivation layer extends directly along the light guides and isolates the organic filter material from the shield layer.

In another aspect, the passivation layer forms an array of reaction recesses. The reaction recesses extend toward or are located within corresponding apertures. For instance, the reaction recesses may have corresponding base surfaces. The base surfaces may be located within the aperture or located a depth into the device base.

In another aspect, the method includes coupling a flow cell to the device base to form a flow channel between the passivation layer and the flow cell.

In another aspect, removing the filter material from the shield layer includes at least one of etching the filter material or chemically polishing the filter material.

In another aspect, the passivation layer includes tantalum pentoxide ($Ta_2O_5$). For example, the passivation layer may include multiple sub-layers in which at least one of the sub-layers includes tantalum pentoxide ($Ta_2O_5$). In a more specific embodiment, the sub-layers may include two tantalum pentoxide layers with a low-temperature film therebetween.

In another aspect, the device base has guide regions that include substrate material prior to forming the guide cavities in which adjacent guide regions are separated by circuitry regions that include the device circuitry. Forming the guide cavities may include removing the substrate material of the guide regions.

In another aspect, the device base may include peripheral crosstalk shields that surround the guide regions prior to forming the guide cavities. The crosstalk shields may at least partially surround the corresponding light guides after the light guides are formed. The crosstalk shields may be configured to reduce optical crosstalk between adjacent light sensors.

In an embodiment, a biosensor is provided that includes a device base having a sensor array of light sensors and a guide array of light guides. The device base has an outer surface. The light guides have input regions that are configured to receive excitation light and light emissions generated by biological or chemical substances proximate to the outer surface. The light guides extend into the device base from the input regions toward corresponding light sensors and have a filter material that is configured to filter the excitation light and permit the light emissions to propagate toward the corresponding light sensors. The device base includes device circuitry electrically coupled to the light sensors and configured to transmit data signals based on photons detected by the light sensors. The biosensor also includes a shield layer that extends along the outer surface of the device base. The shield layer has apertures that are positioned relative to the input regions of corresponding light guides such that the light emissions propagate through the apertures into the corresponding input regions. The shield layer extends between adjacent apertures and is configured to block the excitation light and the light emissions incident on the shield layer between the adjacent apertures.

In an embodiment, a biosensor is provided that includes a device base having a sensor array of light sensors and a guide array of light guides. The device base has an outer surface. The light guides are configured to receive excitation light and light emissions generated by biological or chemical substances proximate to the outer surface. Each of the light guides extends into the device base along a central longitudinal axis from an input region of the light guide toward a corresponding light sensor of the sensor array. The light guide includes a filter material that is configured to filter the excitation light and permit the light emissions to propagate therethrough toward corresponding light sensors. The device base includes device circuitry that is electrically coupled to the light sensors and are configured to transmit data signals based on photons detected by the light sensors. The device base includes peripheral crosstalk shields located therein that surround corresponding light guides of the guide array. The crosstalk shields at least partially surrounding the corresponding light guides about the respective longitudinal axis to at least one of block or reflect errant light rays to reduce optical crosstalk between adjacent light sensors.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings. Also, it is to be understood that phraseology and terminology used herein with reference to device or element orientation (such as, for example, terms like "above," "below," "front," "rear," "distal," "proximal," and the like) are only used to simplify description of one or more embodiments described herein, and do not alone indicate or imply that the device or element referred to must have a particular orientation. In addition, terms such as "outer" and "inner" are used herein for purposes of description and are not intended to indicate or imply relative importance or significance.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the presently described subject matter without departing from its scope. While the dimensions, types of materials and coatings described herein are intended to define the parameters of the disclosed subject matter, they are by no means limiting and are exemplary embodiments. Many other embodiments will be apparent to those of skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112, sixth paragraph, unless and until such claim limitations expressly use the phrase "means for" followed by a statement of function void of further structure.

The following claims recite aspects of certain embodiments of the inventive subject matter and are considered to be part of the above disclosure. These aspects may be combined with one another.

What is claimed is:

1. An apparatus, comprising:
a flow cell; and
a detection device having the flow cell coupled thereto, the flow cell and the detection device forming a flow channel, the detection device including:
a device base having a sensor array of light sensors and a guide array of light guides, each of the light guides extending into the device base from an input region of the light guide, the light guides including a filter material,
wherein the device base includes peripheral crosstalk shields located therein that are positioned relative to the light guides.

2. The apparatus of claim 1, wherein the detection device includes an outer surface and further comprising a passivation layer that extends over the outer surface of the device base.

3. The apparatus of claim 2, wherein the passivation layer forms an array of reaction recesses having corresponding reaction sites.

4. The apparatus of claim 3, further comprising a thermal element that is to transfer thermal energy into the flow channel.

5. The apparatus of claim 3, further comprising a thermal element that is to transfer thermal energy out of the flow channel.

6. The apparatus of claim 3, wherein each light sensor aligns with a single light guide and a single reaction site.

7. The apparatus of claim 1, wherein the flow cell includes a sidewall and a cover supported by the sidewall.

8. The apparatus of claim 7, wherein the cover includes a transparent material.

9. The apparatus of claim 1, wherein the flow cell and the light sensors are coupled together in a substantially unitary structure.

10. The apparatus of claim 1, wherein the crosstalk shields surround the input regions of the light guides.

11. The apparatus of claim 1, wherein the crosstalk shields at least partially surround the light guides.

12. The apparatus of claim 1, wherein a plurality of the crosstalk shields surround each light guide.

13. The apparatus of claim 12, wherein the plurality of the crosstalk shields that surround each light guide are spaced by a gap.

14. The apparatus of claim 12, wherein the plurality of the crosstalk shields are spaced by gaps.

15. The apparatus of claim 14, wherein a size of the gaps are substantially equal to one another.

16. The apparatus of claim 1, wherein the crosstalk shields include crosstalk rings that circumferentially surround the light guides.

17. The apparatus of claim 1, wherein the crosstalk shields directly abut the light guides.

18. The apparatus of claim 1, further comprising a shield layer extending between the flow channel and the device base.

19. The apparatus of claim 18, wherein the shield layer comprises an array of apertures that are positioned relative to the input regions of the light guides.

* * * * *

UNITED STATES PATENT AND TRADEMARK OFFICE
CERTIFICATE OF CORRECTION

| | |
|---|---|
| PATENT NO. | : 11,719,637 B2 |
| APPLICATION NO. | : 17/405379 |
| DATED | : August 8, 2023 |
| INVENTOR(S) | : Zhong et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 147 days.

Signed and Sealed this
Twelfth Day of November, 2024

Katherine Kelly Vidal
*Director of the United States Patent and Trademark Office*